United States Patent
Tuomanen et al.

(10) Patent No.: US 6,495,139 B2
(45) Date of Patent: *Dec. 17, 2002

(54) IDENTIFICATION AND CHARACTERIZATION OF NOVEL PNEUMOCOCCAL CHOLINE BINDING PROTEIN, CBPG, AND DIAGNOSTIC AND THERAPEUTIC USES THEREOF

(75) Inventors: Elaine I. Tuomanen, Germantown; Khoosheh Gosink, Cordova; Robert Masure, Germantown, all of TN (US)

(73) Assignee: St. Jude Children's research Hospital, Memphis, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/287,070

(22) Filed: Apr. 6, 1999

(65) Prior Publication Data

US 2002/0041881 A1 Apr. 11, 2002

Related U.S. Application Data

(63) Continuation-in-part of application No. 09/196,389, filed on Nov. 19, 1998, now abandoned.

(51) Int. Cl.[7] .................. A61K 39/02; A61K 39/00; A61K 39/09; C07K 7/00; C07K 1/00
(52) U.S. Cl. .................. 424/190.1; 424/184.1; 424/185.1; 424/244.1; 530/300; 530/324; 530/350
(58) Field of Search .................. 424/184.1, 185.1, 424/190.1, 244.1; 530/300, 324, 350

(56) References Cited

FOREIGN PATENT DOCUMENTS

| WO | WO 97/41151 | | 11/1997 |
| WO | 97/43303 | * | 11/1997 |
| WO | 98/18930 | * | 5/1998 |
| WO | WO 98/21337 | | 5/1998 |

OTHER PUBLICATIONS

Houghten et al. (Vaccines, 1986, Edited by Fred Brown: Cold Spring Harbor Laboratory).*
(Bowie et al. Science, vol. 247: 1990; p. 1306; p. 1308).*
Appelbaum, Clin. Infect. Dis. 15:77–83, 1992.
Berry et al., Microb Pathog, 12:87–93, 1992.
Briese et al., Eur J Biochem., 146: 417–27, 1985.
Cole et al., Monoclonal Antibodies and Cancer Therapy, Alan R. Liss pp. 77–96, 1985.
Cundell et al.,Infect. Immun., 63(3): 757–61, 1995.
Cundell et al., Microb Pathog, 17:361–74, 1994.
Cundell et al., Nature, 377:435–38, 1995.
Diaz et al., J. Bacteriol. 174:5516–25, 1992.
Garcia et al., Gene 86:81–88, 1990.
Hoepelman et al., Infect. Immun. 60:1729–33, 1992.
Huse et al., Science 246:1275–81, 1989.
Idanpaan–Heikkila et al., J Infect. Dis. 176:704–12, 1997.
Kazmierski et al., J. Am. Chem. Soc. 113:2275–83, 1991.
Neuberger et al., Nature 312:604–8, 1984.
Noren et al., Science 244:182–88, 1989.
Ponsanti et al., Tetrahedron 46:8255–66, 1990.
Romero et al., Microb. Lett. 108:87–92, 1993.
Ronda et al., Eur. J. Biochem. 164:621–4, 1987.
Rosenow et al., Mol Microbiol., 25: 819–29, 1997.
Sanchez–Beato, et al., J. Bacterial. 177:1098–1103, 1995.
Sanchez–Puelles et al., Gene, 89: 69–75, 1990.
Shapiro et al., NEJM 325:1453–60, 1991.
Talkington et al., Microb. Pathog. 13:343–55, 1992.
Tomasz et al, Microbiology, Schlessinger ed., p 202–15.
Tomasz, The Target of Penicillin, Hackenback et al. eds, pp. 155–172.
Tuomanen et al. NEJM 322:1280–1284, 1995.
Von Eichel–Streiber et al., Gene 96:107–13.
Von Eichel–Streiber et al., J. Bacteriol. 174:6707–10, 1992.
Wieser et al., Infect. Immun., 62(6): 2582–89.
Wren et al., Mol. Microbiol. 5:797–803, 1991.
Yother and White, J. Bacteriol. 176:2976–85, 1994.
Yother et al., J. Bacteriol. 174:610, 1992.
Zee–Cheng et al., Biophys. Biochem. Res. Commun. 94:1128–32, 1980.

* cited by examiner

Primary Examiner—Lynette R. F. Smith
Assistant Examiner—Padma Baskar
(74) Attorney, Agent, or Firm—Alston & Bird LLP

(57) ABSTRACT

The present invention provides isolated polypeptides comprising an amino acid sequence of a choline binding protein CbpG. This invention provides an isolated polypeptide comprising an amino acid sequence of a choline binding polypeptide CbpG or N-terminal CbpG truncate, including analogs, variants, mutants, derivatives and fragments thereof This invention further provides an isolated immunogenic polypeptide comprising an amino acid sequence of a choline binding protein CbpG. This invention provides an isolated nucleic acid encoding a polypeptide comprising an amino acid sequence of a choline binding protein CbpG. This invention provides pharmaceutical compositions, vaccines, and diagnostic and therapeutic methods of use of the isolated polypeptides and nucleic acids. Assays for compounds which alter or inactivate the polypeptides of the present invention for use in therapy are also provided.

6 Claims, 11 Drawing Sheets

```
                                                                                                                        1560
AAGCAGCTCCATGGTACTACTCTAAATCCAGCAACTGGCAATTATGCAAATATCAGTTGGCAATATCTAGTAATAGATAGTACTACCTCCATTGTCAGGAGCTATGGCTCAACTGGCTGGTATAAGGAAGCT
----+----+----+----+----+----+----+----+----+----+----+----+----+----+----+----+----+----+----+----+----+----+----+----+----+----+
TTCGTCGAGGTACCATGATGAGATTTAGGTCGTTGACCGTTAATACGTTTGTCCAACCGTTATAGATCATTATCGATGGAGGTAAGCAGTCCTCGATACCGAGTTGACCGACCATATTCCTTCCGA

LysAlaAlaProTrpTyrTyrLeuAsnProAlaThrGlyIleMetGlnThrGlyTrpTyrLeuHisSerSerGlyAlaMetAlaThrGlyTrpTyrLysGluGly
                                                                                                    CbpF
                                                                                                                        1690
CAACTTGTACTACTATCTAGATGCTGAAAATGTGATATAGAACTGGCTGGCAAAACCTTGGGAACAAATGTACTATCCGTTCATCAGGAGCTATGGCACTGTTGGTATCAGGAAAGTTCGACTTG
----+----+----+----+----+----+----+----+----+----+----+----+----+----+----+----+----+----+----+----+----+----+----+----+----+
GTTGAACCATGATGATAGATCTACGACTTTTACCACTATACTCTTGACCGACCGTTTGAACCCTTGTTTGGAACATGATAGGCAAGTAGTCCTCGATACCGTGACCAACCATAGTCCTTTCAAGCTGAAC

SerThrTyrTyrLeuAspAlaGluAsnGlyAspMetArgThrGlyTrpGlnAsnLeuGlyAsnLysTrpTyrTyrLeuArgSerSerGlyAlaMetAlaThrGlyTrpTyrGlnGluSerSerThrTrp
                                                                                                                        CbpF
                                                                                                                        1820
GTACTATCTAAATGCAAGTAATGGAGATATGAAAAACAGCTGGTTCCAAGTCAATGTAACTGGTACTATGCCTATGATTCAGTGCTCTTAGCTGTTAATACCACAGTAGGTGGTTACTACTTAAACTAT
----+----+----+----+----+----+----+----+----+----+----+----+----+----+----+----+----+----+----+----+----+----+----+----+----+----+
CATGATAGATTTACGTTCATTACCTCTATACTTTTGTCGACCAAGGTTCAGTTACATTGACCATGATACGGATACTAAGTCACAATTATGGTGTCATCCACCAATGATGATTTGATA

TyrTyrLeuAsnGlyValAspSerGlyAlaLeuLeuAlaValAlaAsnThrThrValGlyGlyTyrTyrLeuAsnTyr
                                                                      CbpF

AATGGTGAATGGGTTAAGTAATGAAGGCTTAATTGTAAACTGTGATGGATACTTAACTTTGTATAATAGG    1889
----+----+----+----+----+----+----+----+----+----+----+----+----+
TTACCACTTACCCAATTCATTACTTCCGATTAACATTTGACACTACTATGAATTGAAACATATTATCC

AsnGlyGluTrpValLyster
            CbpF
```

| CbpG | DELETION MUTANTS IN STRAINS | | TRUNCATES | AB RECOGNITION OF | | RAT NOSE COLO | IN VITRO ADHESION TO LNnT | [TRSF w CSP] | LYSIS w DOC |
| | T4 | T4R | | RECOM | CBP PREP | | | | |
| --- | --- | --- | --- | --- | --- | --- | --- | --- | --- |
| CbpG | Y | Y | 20 KD YES | ** | - | DOWN | REDUCED | NORMAL | NORMAL |

FIG. 7

```
ATGTATACAGATAAGAAACAAGTTTTAAGTGATGATGGCATGTTCTTGGATTACCAAGTTGATATACTTTAGAGGGGTCTAGTGGAATCACAGTTTATGATGCTASTCACCGTGTAGTAGGA
----+----+----+----+----+----+----+----+----+----+----+----+----+----+----+----+----+----+----+----+----+----+----+----+ 120
TACATATGTCTATTCTTTGTTCAAAATTCACTACTACCGTACAAGAACCTAATGTTCAACTATGAAATCTCCCAGATCACCTAGATGTCAAATACTAGATSAGTGGCACATCATCCT
```

MetTyrThrAspLysLysGlnValLeuSerAspAspGlyMetPheLeuAspTyrGlnValAspThrLeuGluGlySerGlySerThrValTyrAspAla???HisArgValValGly

```
GTGCATACTTTAGGAGATGGAGCTAATCAAATTAACAGTGCAGTTAAAATTAAATGAACGAAAATTTGCCATTTATTTATTCGGTTCTTAAAGGTTACTCTCTTGAAGGATGGAAGAAAATA
----+----+----+----+----+----+----+----+----+----+----+----+----+----+----+----+----+----+----+----+----+----+----+----+ 240
CACGTATGAAATCCTCTACCTCGATTAGTTTAATTGTCACGTCAATTTAATTAAGCCAAGAATTCCAATGAGAGAACTTCCTACCTTCTTTTAT
```

ValHisThrLeuGlyAspGlyAlaAsnGlnIleAsnSerAlaValLysLeuAsnGluArgAsnLeuProPheIleTyrSerValLeuLysGlyTyrSerLeuGluGlyTrpLysLysIle

```
AATGGTAGTTGGTACCATTATAGACAACAT
----+----+----+----+----+----+ 270
TTACCATCAACCATGGTAATATCTGTTGTA
```

AsnGlySerTrpTyrHisTyrArgGlnHis

FIG. 8

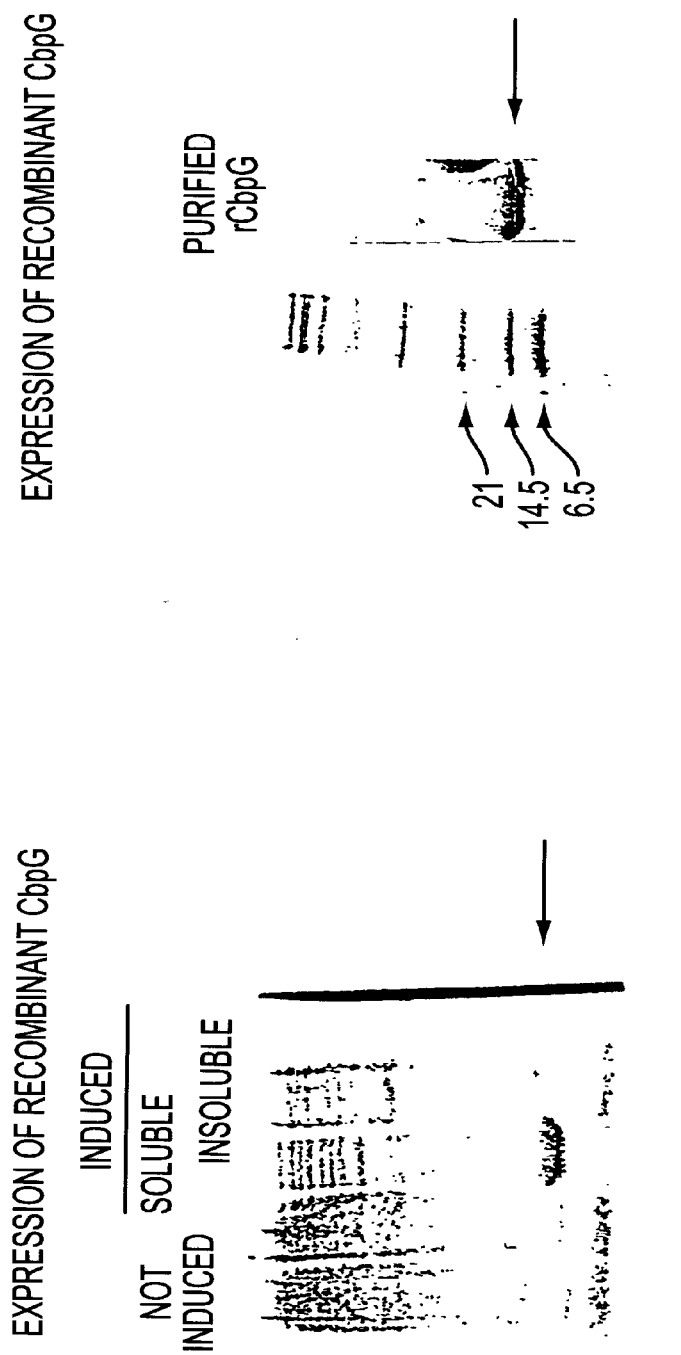

IDENTIFICATION AND CHARACTERIZATION OF NOVEL PNEUMOCOCCAL CHOLINE BINDING PROTEIN, CBPG, AND DIAGNOSTIC AND THERAPEUTIC USES THEREOF

RELATED APPLICATIONS

The present application is a continuation-in-part of application Ser. No. 09/196,389 filed Nov. 19, 1998, now abandoned, of which the instant application claims the benefit of the filing date pursuant to 35 U.S.C. §120, and which is incorporated herein by reference in its entirety.

FIELD OF THE INVENTION

The present invention relates generally to choline binding polypeptides and to nucleic acids encoding such polypeptides. The invention also relates to vaccines which provide protection or elicit protective antibodies to bacterial infection, and to antibodies and antagonists against or inhibitors of such polypeptides for use in diagnosis, therapy and passive immune therapy. In particular, the choline binding polypeptides of the invention are useful as vaccines against Streptococcus, particularly pneumococcus. A choline binding polypeptide of the present invention is also useful as a competitive inhibitor of bacterial adhesion, or to discover small molecule antagonists of adhesion.

BACKGROUND OF THE INVENTION

*Streptococcus pneumoniae* is a gram positive bacteria which is a major cause of invasive infections such as sepsis, meningitis, otitis media and lobar pneumonia (Tuomanen et al *NEJM* 322:1280–1284, 1995). Vaccination has long been an important armament in the arsenal against infectious microorganisms. Prior to the introduction of antibiotics, vaccination was the major hope for protecting populations against viral or bacterial infection. With the advent of antibiotics, vaccination against bacterial infections became less important. However, the emerging problems withantibiotic resistance among such infectious bacteria, including *S. pneumoniae* strains, have raised an urgent need for a better understanding of the pathogenesis of these pathogens and has reestablished the importance of anti-bacterial vaccines (Appelbaum, P.C. (1992) *Clin Infect Dis* 15:77–83).

There are over 90 different types of the pneumococcal organism, each with a different chemical structure of the capsular polysaccharide (i.e., each antigenically distinct). The capsular polysaccharide is a principal known virulence factor of the pneumococcus and induces an antibody response in adults. Current vaccines against *S. pneumoniae* employ mixtures of the capsules of the 23 most common serotypes of this bacterium. After several comprehensive studies there is now overwhelming evidence that this vaccine is approximately 60% efficacious for the general population (Shapiro et al.(1991) *NEJM* 325:1453–60). Importantly, these vaccines are ineffective in individuals most susceptible to pathological infection—the young, the old, and the immune compromised—because of their inability to elicit a T cell immune response. Conjugation of the capsule to a protein permits protection in the younger age group but is inherently limited in the number of capsules that can be conjugated at one time (approximately 5–8 capsules only).

Exported proteins in bacteria participate in many diverse and essential cell functions such as motility, signal transduction, macromolecular transport and assembly, and the acquisition of essential nutrients. For pathogenic bacteria such as *S. pneumoniae*, many exported proteins are virulence determinants that function as adhesins to colonize and thus infect the host, or as toxins to protect the bacteria against the host's immune system (for a review, see Hoepelman and Tuomanen (1992) *Infect Immun* 60:1729–33). One alternative to current vaccines are subunit vaccines in which the antigen, or antigens, include a bacterial surface protein or proteins. These vaccines could overcome the deficiencies of whole bacterial or capsule-based vaccines. Moreover, given the importance of exported or surface proteins to bacterial virulence, these proteins are an important target for therapeutic intervention.

Pneumococci bind avidly to cells of the upper and lower respiratory tract. Like most bacteria, adherence of pneumococci to human cells is achieved by presentation of bacterial surface proteins that bind to eukaryotic cell surface carbohydrates in a lectin-like fashion (Cundell, D. & Tuomanen, E. (1994) *Microb Pathog* 17:361–374). Pneumococci bind to non-inflamed epithelium, a process that can be viewed as asymptomatic carriage. It has been proposed that the conversion to invasive disease involves the local generation of inflammatory factors which, activating the human epithelial cell, change the number and type of receptors available on the human cells (Cundell, D. et al. (1995) *Nature,* 377:435–438). Presented with an opportunity in this new setting, pneumococci appear to take advantage and engage one of these unregulated receptors, the platelet activating factor (PAF) receptor (Cundell et al. (1995) *Nature,* 377:435–438). Within minutes of the appearance of the PAF receptor, pneumococci undergo waves of enhanced adherence and invasion. Inhibition of bacterial binding to activated cells, for instance by soluble receptor analogs, blocks the progression to disease in animal models (Idanpaan-Heikkila, I. et al. (1997) *J. Infect. Dis.,* 176:704–712). Particularly effective in this regard are soluble carbohydrates containing lacto-N-neotetraose with or without an additional sialic acid, which prevent pneumococcal attachment to human cells in vitro and prevent colonization in the lung in vivo.

Pneumococci display a family of surface proteins which bind to the bacterial surface by non-covalent association to the cell wall teichoic acid or lipoteichoic acid, specifically through its terminal component phosphorylcholine. The surface of *Streptococcus pneumoniae* is decorated with twelve types of these choline binding proteins (Cbps). The Cbps are represented by a family of molecules which decorate the surface of pneumococcus, each serving a unique function but bound to the surface by a common element. These proteins consist of an N-terminal activity domain and a repeated C-terminal signature choline binding domain that contains two to greater than ten repeats of a 20 amino acid choline binding sequence that binds to phosphoryl choline and that anchors these molecules to the surface of the bacteria. This motif has been identified in the C-terminal regions of a secreted glycoprotein from *Clostridium acetobutylicum* NCIB 88052 [Sanchez-Beato, et al., *J. Bacteriol.* 177:1098–1103 (1995)], toxins A and B from *Clostridium difficile* [Von Eichel-Streiber and Sauerbom, *Gene* 96:107–13 (1990); Von Eichel-Streiber et al., *J. Bacteriol.* 174:6707–6710 (1992)], a glucan-binding protein from *Streptococcus mutans,* several glycosyltransferases from *Streptococcus downei* and *S. mutans,* the murein hydrolase (LytA) from pneumococcus and pneumococcal lytic phage [Ronda et al., *Eur. J. Biochem.* 164:621–4 (1987); Diaz et al., *J. Bacteriol.* 174:5516–25 (1992); Romero et al., *Microb. Lett.* 108:87–92 (1993); Yother and White, J. Bacteriol. 176:2976–85 (1994)], and a surface antigen (PspA) also from pneumococcus. The known pneumococcal Cbp family members are CbpA, LytA and PspA.

The choline binding domain was recognized and fully characterized by Lopez et al. in his studies of the autolytic enzyme, LytA (Ronda et al. (1987) Eur. J. Biochem, 164:621–624). From studies of the sequences of the recognized choline binding proteins, consensus sequences have been reported, most particularly that of Garcia et al: GWLKDNGSWYYLNANGAMAT (SEQ ID NO:26) (Garcia, P. et al (1990) Gene 86:81–88; Wren B. et al (1991)Mol Microbiol 5:797–803); Sanchez-Beato, A. R. et al (1995) J Bacteriol 177:1098–1103).

Teichoic acid (TA), an integral part of the cell wall of Streptococcus pneumoniae, contains many terminal phosphorylcholine moieties. Choline affinity chromatography or Mono-Q Sepharose, a close relative of choline, were used to purify the CBPs. Previous studies have shown that PspA, as well as one other surface exposed protein, LytA, the autolytic amidase, bind in a choline-dependent manner. PspA, a protein having a molecular weight of 84 kDa, and which is highly variable, is released from the cell surface with high choline concentration (at least about 2% to about 10%). The function of PspA is unknown. LytA, or autolysin, is a 36 kDa protein, which lyses the pneumococcal cell wall (self lysis), but is not released from the cell by growth in high concentrations of choline, by washing in 10% choline, or by growth in ethanolamine. Reports on choline binding proteins include those by Sanchez-Puelles et al Gene 89:69–75 (1990), Briese and Hakenback Eur. J. Biochem. 146:417–427, Yother and White J. of Bacteriol. 176:2976–2985, Sanchez-Beato et al J. of Bacteriol. 177:1098–1103, and Wren Micro. Review Mol. Microbiol. 5:797–803 (1991), which are hereby incorporated by reference in their entirety.

CbpA is an adhesin (ligand) for the glycoconjugate containing receptors present on the surface of eucaryotic cells. CbpA is a 663 amino acid protein with an apparent molecular mass of 112 KDa. CbpA has been shown to be critical to pneumococcal colonization and attachment to human cells. Mutants with defects in cbpA show reduced virulence in the infant rat model for nasopharyngeal colonization and fail to bind to eucaryotic cells found at the site of infection and to glycoconjugates that bind pneumococcus. The CbpA protein cross reacts with human convalescent antisera, and antisera to the Cbps passively protected mice in a model for sepsis. Since the process of colonization and the progression to disease depend on pneumococcal attachment to human cells as a primary step, interruption of the function of surface choline binding proteins or the choline binding domain, for instance by cross reactive antibody or by inhibition with a competitive peptide mimicking this domain, may be relevant to blocking disease.

Choline-binding proteins for anti-pneumococcal vaccines are disclosed in International Patent Application WO 97/41151 of Masure, et al, which claims priority to U.S. patent application Ser. No. 08/642,250, which are hereby incorporated by reference in their entirety. The International patent Application WO 97/41151 discloses partial polypeptide sequences of certain putative choline binding proteins and the polypeptide sequence of CbpA.

The cell wall associated choline binding protein, LytA, a murein amidase, is an autolysin that is responsible for remodeling the cell wall, the separation of daughter cells, cell death in stationary phase and penicillin induced cell lysis. Expansion of the cell wall during bacterial growth and splitting of the septum for cell separation require enzymes that cleave the peptidoglycan network enclosing the cell. In addition to acting as spacemaker enzymes for cell wall growth, some of these enzymes act as autolysins, thereby representing potentially suicidal enzymes. Regulation of these enzymes is therefore important and must take into consideration their extracytoplasmic location. Unlike other bacteria which have multiple autolysins, S. pneumoniae has only one major autolysin, LytA. Antibiotics such as penicillin induce bacteriolysis by interfering with the control of the endogenous autolysins (Tomasz & Holtje, 1977, in Microbiology, D. Schlessinger, ed., pp. 202–215; Tomasz, 1983, in The Target of Penicillin, R. Hackenback et al eds., pp. 155–172). Although the binding of antibiotics to cell wall synthetic enzymes has been well characterized, the mechanism by which it induces autolysin mediated cell wall degradation is unknown. Tolerance to such antibiotics arises if the bacterial autolysins are not triggered as the antibiotic inhibits the cell wall synthetic machinery. The question of whether antibodies raised against LytA are protective against infection by S. pneumoniae and its requirement for virulence remains controversial. In some cases, loss of LytA by deletion leads to less virulence, while others report no effect (Berry, A. M. et al (1992) Microb Pathog 12:87–93).

PspA has been reported to be a candidate for a S. pneumoniae vaccine as it has been found in all pneumococci to date [see Yother et al., J. Bacteriol., 174:610 (1992)]; the purified protein can be used to elicit protective immunity in mice; and antibodies against the protein confer passive immunity in mice [Talkington et al., Microb. Pathog. 13:343–355 (1992)]. However, PspA demonstrates antigenic variability between strains in the N-terminal half of the protein, which contains the immunogenic and protection eliciting epitopes (Yother et al., supra). This protein does not represent a common antigen for all strains of S. pneumoniae, and therefore is not an optimal vaccine candidate.

As described above, each Cbp, while being bound to the surface by a common element, the choline binding domain, serves a unique function. This particular function is largely determined by the unique N-terminal activity domain of each Cbp. N-terminal domain fragments of Cpbs, particularly CbpA, have been shown to have activity in blocking adherence and are candidates for immunogenic vaccines, independent of the C-terminal choline binding domain. In particular, Tuomanen et al, U.S. Ser. No. 09/056,019, which is hereby incorporated herein by reference in its entirety, provides isolated polypeptides comprising N-terminal choline binding protein A truncates, particularly wherein the polypeptides do not bind to choline. Vaccines comprising such N-terminal truncates, DNA encoding such truncates, or antibodies directed against such truncates are also described in U.S. Ser. No. 09/056,019.

An additional surface exported protein that affects adherence and represents a virulence determinant for pneumococcus, ZmpB, has been identified and described by R. Novak and R. Masure in U.S. Ser. No. 09/096,336 filed Jun. 11, 1998 which is hereby incorporated by reference in its entirety. ZmpB is a zinc metalloprotease, dependent on $Zn^{2+}$ for functional activity. zmpB mutants show loss of adherence and colonization and are defective in the autolytic pathway. A mutation in zmpB selectively alters the production of CbpA and generates covalently modified LytA. ZmpB is proposed to be a master regulatory protein that controls the expression of multiple Cbps critical for bacterial survival in the human host. ZmpB is a candidate for an S. pneumoniae vaccine or as one component of a multicomponent vaccine.

The deficiencies of whole bacterial or capsule-based vaccines and the emerging problems with antibiotic resistance among infectious bacteria, including *S. pneumoniae* strains, have raised an urgent need for alternative effective vaccines and therapies. The invention herein fills such a need in providing protective vaccines and therapies.

The citation of references herein shall not be construed as an admission that such is prior art to the present invention.

SUMMARY OF THE INVENTION

In its broadest aspect, the present invention encompasses isolated polypeptides comprising an amino acid sequence of a choline binding protein, CbpG.

The present invention is directed to an isolated polypeptide comprising an amino acid sequence of a pneumococcal choline binding protein, CbpG and wherein such polypeptide contains a choline binding domain sequence which is homologous to SEQ ID NO:1.

The present invention provides an isolated polypeptide comprising an amino acid sequence of a pneumococcal choline binding protein, CbpG wherein such polypeptide contains a choline binding domain sequence which is homologous to GWLKDNGSWYYLNANGAMAT (SEQ ID NO:10).

The present invention further provides an isolated polypeptide comprising an amino acid sequence of an N-terminal CbpG choline binding protein truncate. The present invention provides an N-terminal CbpG truncate comprising the amino acid sequence as set forth in SEQ ID NO: 11. The invention particularly provides an N-terminal CbpG truncate consisting of amino acids 1–90 of the CbpG choline binding protein. In a further embodiment, the N-terminal CbpG truncate comprises less than amino acids 1–90 of the CbpG choline binding protein.

In a still further aspect, the present invention extends to vaccines based on the choline binding proteins described herein.

The present invention provides an isolated polypeptide comprising an amino acid sequence of a choline binding protein CbpG. The polypeptide comprises the amino acid sequence as set forth in SEQ ID NO:2 including fragments, mutants, variants, analogs, or derivatives, thereof The isolated polypeptide is suitable for use in immunizing animals and humans against bacterial infection, preferably pneumococci.

The present invention further provides an isolated polypeptide comprising an amino acid sequence of a N-terminal CbpG choline binding protein truncate, particularly wherein the polypeptide does not bind to choline. This invention provides an isolated immunogenic polypeptide comprising an amino acid sequence comprising an N-terminal truncate of a choline binding protein CbpG. In a particular embodiment, this invention provides an isolated immunogenic N-terminal CbpG truncate polypeptide comprising the amino acid sequence as set forth in SEQ ID NO:11. The present invention further particularly provides an immunogenic N-terminal CbpG truncate polypeptide consisting of amino acids 1–90 of CbpG, or of less than amino acid 1–90 of CbpG.

In a still further aspect, the present invention extends to an immunogenic choline binding protein polypeptide CbpG or a fragment thereof The present invention also extends to immunogenic choline binding protein polypeptides wherein such polypeptides comprise a combination of at least two choline binding polypeptides selected from the group consisting of CbpG and at least one other choline binding polypeptide, including fragments thereof and N-terminal truncates thereof.

The present invention also relates to isolated nucleic acids, such as recombinant DNA molecules or cloned genes, or degenerate variants thereof, mutants, analogs, or fragments thereof, which encode the isolated polypeptide or which competitively inhibit the activity of the polypeptide. The present invention further relates to isolated nucleic acids, such as recombinant DNA molecules or cloned genes, or degenerate variants thereof, mutants, analogs, or fragments thereof, which encode the choline binding protein CbpG. Preferably, the isolated nucleic acid, which includes degenerates, variants, mutants, analogs, or fragments thereof, has a sequence as set forth in SEQ ID NO:3. In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present invention, and more particularly, the DNA sequences or fragments thereof determined from the sequences set forth above.

In a particular embodiment, the nucleic acid has the sequence selected from the group comprising SEQ ID NO:3; a sequence complementary to SEQ ID NO:3; or a homologous sequence which is substantially similar to SEQ ID NO:3. In a further embodiment, the nucleic acid has the sequence consisting of SEQ ID NO:3.

The present invention further relates to isolated nucleic acids encoding an N-terminal choline binding protein truncate, particularly wherein the encoded polypeptide does not bind to choline. This invention particularly provides isolated nucleic acids encoding N-terminal choline binding protein truncates of choline binding protein CbpG. The invention further provides a nucleic acid encoding an N-terminal CbpG truncate comprising SEQ ID NO:12, a sequence complimentary to SEQ ID NO:12, or a homologous sequence which is substantially similar to SEQ ID NO:12. In a further embodiment, the nucleic acid encoding the N-terminal CbpG truncate has the sequence consisting of SEQ ID NO:12.

In a particular embodiment, the nucleic acid encoding an N-terminal CbpG truncate is capable of encoding amino acids 1–90 of CbpG. In a still further embodiment, the nucleic acid encoding an N-terminal CbpG truncate encodes a truncate smaller than amino acids 1–90 of CbpG.

Nucleic acid vaccines or DNA vaccines utilize nucleic acids encoding particular immunogenic polypeptides to induce immunity in a host against such encoded immunogenic vaccines. Such nucleic acid based vaccines can be used directly as naked DNA, or can utilize well recognized expression vectors or retroviral vectors, as more particularly described herein, to encode such immunogenic polypeptide on expression in the host cell. Methods to generate and utilize such any such nucleic acid vaccines or DNA vaccines are well known in the art.

The present invention relates to nucleic acid vaccines or DNA vaccines comprising nucleic acids encoding immunogenic polypeptides of a choline binding protein CbpG. The present invention relates to nucleic acid vaccines or DNA vaccines comprising nucleic acids encoding immunogenic polypeptides of choline binding protein CbpG or a fragment thereof or any combination of CbpG with at least one other choline binding polypeptide. Still further, this invention provides nucleic acid vaccines or DNA vaccines comprising nucleic acids encoding an immunogenic N-terminal polypeptide of choline binding protein CbpG.

Antibodies against the isolated polypeptide include naturally raised and recombinantly prepared antibodies. These may include both polyclonal and monoclonal antibodies prepared by known genetic techniques, as well as bi-specific (chimeric) antibodies, and antibodies including other functionalities suiting them for diagnostic use. Such antibodies can be used in immunoassays to diagnose infection with a particular strain or species of bacteria. The antibodies can also be used for passive immunization to treat an infection with Gram positive bacteria, particularly pneumococcus. These antibodies may also be suitable for modulating bacterial adherence including but not limited to acting as competitive agents.

It is still a further object of the present invention to provide a method for the treatment of mammals to control the amount or activity of the pneumococci bacteria or its subunits, so as to treat or avert the adverse consequences of invasive, spontaneous, or idiopathic pathological states. This invention provides pharmaceutical compositions for use in therapeutic methods which comprise or are based upon the isolated polypeptides, their subunits or their binding partners.

The invention further provides pharmaceutical compositions, vaccines, and diagnostic and therapeutic methods of use thereof The invention provides pharmaceutical compositions comprising a choline binding polypeptide CbpG and a pharmaceutically acceptable carrier. The present invention further provides pharmaceutical compositions comprising a choline binding polypeptide of a choline binding protein CbpG, or a fragment thereof or any combination of CbpG with at least one other choline binding polypeptide, and a pharmaceutically acceptable carrier. Still further, this invention provides pharmaceutical compositions comprising N-terminal polypeptide of choline binding protein CbpG and a pharmaceutically acceptable carrier.

The invention further relates to a vaccine for protection of an animal subject from infection with a Gram positive bacterium comprising a vector containing a gene encoding a choline binding protein CbpG of a Gram positive bacterium operatively associated with a promoter capable of directing expression of the gene in the subject. Preferably, such vaccine contains a gene encoding a choline binding protein CbpG of pneumococcus.

In another aspect, the invention is directed to a vaccine for protection of an animal subject from infection with a Gram positive bacterium, most preferably pneumococcus, comprising an immunogenic amount of a choline binding protein CbpG, or a derivative or fragment thereof. Such a vaccine may contain the protein conjugated covalently to a bacterial capsule or capsules from one or more strains of bacteria, including pneumococcus. In one such embodiment, at least one of the bacterial capsules is derived from a mutant strain of bacteria which is non-adherent and non-virulent. In a further such embodiment, the non-adherent and non-virulent bacteria is a pneumococcus and is a CbpG mutant bacteria. Such non-adherent and non-virulent CbpG mutant bacteria can further be utilized in expressing other immunogenic or therapeutic proteins for the purposes of eliciting immune responses to any such other proteins in the context of vaccines and in other forms of therapy.

The invention further provides a cbpG mutant bacteria which is non-adherent to nasopharyngeal cells or to lung cells. Particularly, such cbpG mutant is a gram positive bacteria. More particularly, such cbpG mutant is Streptococcus. Most particularly, such cbpG mutant is *Streptococcus pneumoniae*.

The invention includes an assay system for screening of potential compounds effective to modulate the choline binding activity of the choline binding protein of the present invention. The invention more particularly includes an assay system for screening of potential compounds effective to modulate the choline binding activity of the choline binding protein CbpG. In one instance, the test compound, or an extract containing the compound, could be administered to a cellular sample expressing the choline binding protein CbpG to determine the compound's effect upon the activity of the protein by comparison with a control. In a further instance the test compound, or an extract containing the compound, could be administered to a cellular sample expressing the choline binding protein CbpG, to determine the compound's effect upon the activity of the protein, and thereby on adherence of said cellular sample to host cells, by comparison with a control.

The invention includes an assay system for screening of potential compounds effective to modulate the activity of the N-terminal domain of the choline binding protein of the present invention. The invention more particularly includes an assay system for screening of potential compounds effective to modulate the activity of the N-terminal domain of CbpG. In one instance, the test compound, or an extract containing the compound, could be administered to a cellular sample expressing the choline binding protein CbpG to determine the compound's effect upon the activity of the protein by comparison with a control. In a further instance the test compound, or an extract containing the compound, could be administered to a cellular sample expressing the choline binding protein CbpG to determine the compound's effect upon the activity of the protein, and thereby on adherence of said cellular sample to host cells, by comparison with a control. In another instance, the test compound, or an extract containing the compound, could be administered to a cellular sample expressing an N-terminal truncate (which lacks the C-terminal choline binding domain) of the choline binding protein CbpG to determine the compound's effect upon the activity of the protein by comparison with a control. In a particular such instance, the cellular sample expresses an N-terminal CbpG truncate comprising amino acids 1–90 of CbpG or a smaller N-terminal truncate comprising less than amino acids 1–90 of CbpG. In a further such instance, the N-terminal CbpG truncate comprises the amino acid sequence set out in SEQ ID NO:11.

Other objects and advantages will become apparent to those skilled in the art from a review of the following description which proceeds with reference to the following illustrative drawings.

BRIEF DESCRIPTION OF THE DRAWINGS

FIG. 1 depicts the nucleic acid and amino acid sequence of the C-terminal 180 amino acids of CbpA. (amino acids 615–695).

FIGS. 2A–C depicts the nucleotide sequence and amino acid sequence for both CbpF and CbpG.

FIG. 3 depicts the nucleotide sequence for CbpG including upstream promoter region.

FIG. 7 presents a tabulation of characterization studies of CbpG. The tabulation indicates the following: size of recombinantly prepared protein in kD; availability of N-terminal truncates (wherein the C-terminal choline binding domain is removed) (yes indicates available, blank indicates not available); recognition of recombinant protein by polyclonal anti-CbpG antibody on a Western Blot of a 4–15% gradient SDS-PAGE ( indicates recognition, - indicates no recognition); recognition of the corresponding CbpG protein on a Western Blot of a native choline binding protein preparation run on a 4–15% gradient SDS-PAGE ( indicates recognition, - indicates no recognition); effects of a knockout of CbpG in rat nose colonization studies (N indicates no significant effect, Down indicates a significant reduction in colonization); In vitro adhesion to LNnT shows the effects of a knockout of CbpG on in vitro adhesion to LNnT (Lacto N-neotetraose-HSA) (reduced indicates significantly reduced from wild type); TRSF w CSP depicts the effect of the knockout of CbpG on transformation of *S. pneumoniae* in the presence of competence stimulating protein (Normal indicates no effect; nd indicates not done); LYSIS w DOC provides the effect of the knockout of CbpG on the ability of Deoxycholate to lyse the particular knockout strains (Normal indicates no effect).

FIG. 8 depicts the nucleic acid sequence and amino acid sequence for the N-terminal CbpG truncate.

FIG. 9A depicts the expression of recombinant CbpG truncate and migration in SDS gel electrophoresis as detected by Coomassie blue staining. Lanes represent "not induced" and the "induced" soluble or insoluble fraction after induction of expression.

FIG. 9B depicts migration of purified recombinant CbpG truncate on SDS gel electrophoresis as detected by Coomassie blue staining. The CbpG truncate size is 13 kD as compared to MW Standards and is found in abundance in the soluble fraction of the cell preparation.

DETAILED DESCRIPTION

Figure 4:
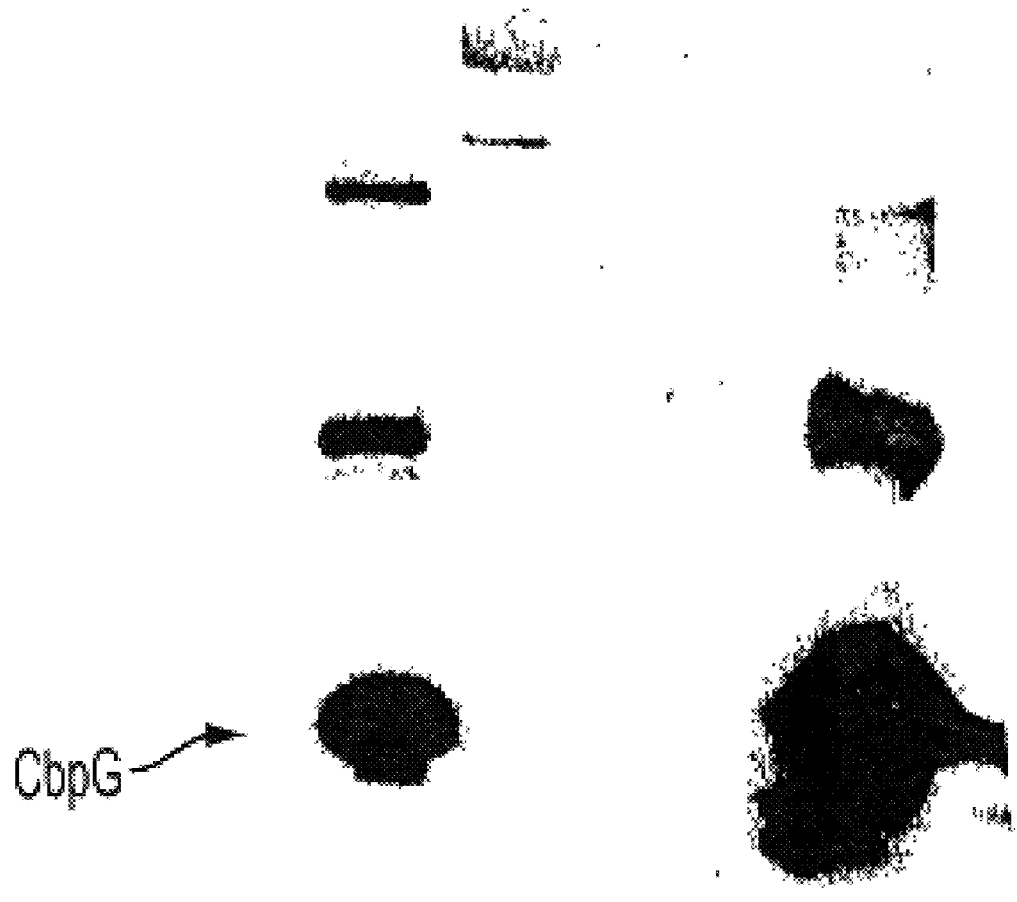
FIG. 4 depicts a Western Blot of a 10% SDS-PAGE on which choline binding proteins were separated and reacted with polyclonal antibody directed against CbpG. Lane 1 is a ladder of recombinant choline binding proteins. Lane 2 is a Cbp preparation from *S. pneumoniae* Type 4. Lane 3 is a choline soak of *S. pneumoniae* Type 4. Lane 4 is recombinant CbpG.

The present invention is directed to an isolated polypeptide comprising an amino acid sequence of a choline binding protein CbpG. The present invention further provides an isolated polypeptide comprising an amino acid sequence of a pneumococcal choline binding protein CbpG wherein such polypeptide contains a choline binding domain sequence which is homologous to SEQ ID NO:1. The present invention further provides an isolated polypeptide comprising an amino acid sequence of a pneumococcal choline binding protein CbpG, wherein such polypeptide contains a choline binding domain sequence which is homologous to GWLKDNGSWYYLNANGAMAT (SEQ ID NO:10).

The present invention is directed to an isolated polypeptide comprising an amino acid sequence of a choline binding polypeptide CbpG. The polypeptides of the present invention are suitable for use in immunizing animals against pneumococcal infection. These polypeptide or peptide fragments thereof, when formulated with an appropriate adjuvant, are used in vaccines for protection against pneumococci, and against other bacteria with cross-reactive proteins.

This invention provides an isolated polypeptide comprising an amino acid sequence of a choline binding protein CbpG. In a particular embodiment the polypeptide has the amino acid sequence as set forth in SEQ ID NO:2 including fragments, mutants, variants, analogs, or derivatives, thereof.

This invention provides an isolated polypeptide comprising an amino acid sequence of a choline binding protein CbpG as set forth in FIG. 2. In one embodiment the polypeptide is an analog, fragment, mutant, derivative or variant thereof.

This invention further provides an isolated polypeptide comprising an amino acid sequence of a N-terminal choline binding protein truncate, particularly wherein the polypeptide does not bind to choline. This invention particularly provides an isolated immunogenic polypeptide comprising an amino acid sequence of a N-terminal choline binding protein CbpG truncate. In a particular embodiment, this invention provides an N-terminal CbpG truncate comprising amino acids 1–90 of CbpG or an immunogenic fragment thereof. In a further embodiment, the N-terminal CbpG truncate may comprise less than amino acids 1–90. The invention particularly provides an N-terminal CbpG truncate comprising the amino acids set out in SEQ ID NO: 11.

The identity or location of one or more amino acid residues may be changed or modified to include variants such as, for example, deletions containing less than all of the residues specified for the protein, substitutions wherein one or more residues specified are replaced by other residues and additions wherein one or more amino acid residues are added to a terminal or medial portion of the polypeptide. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

Further, this invention provides an isolated polypeptide comprising an amino acid sequence of a choline binding protein CbpG, wherein the polypeptide has the amino acid sequence set forth in SEQ ID NO:2.

This invention is directed to a polypeptide comprising an amino acid sequence of a choline binding protein CbpG, wherein the amino acid sequence is set forth in FIG. 2 and in SEQ ID NO:2.

This invention provides an isolated polypeptide comprising an amino acid sequence of a choline binding protein CbpG, wherein the polypeptide has choline binding activity. In one embodiment the polypeptide has the amino acid sequence as set forth in SEQ ID NO:2 including fragments, mutants, variants, analogs, or derivatives, thereof As defined herein, "adhesion" means noncovalent binding of a bacteria to a human cell or secretion that is stable enough to withstand washing.

The term "choline binding protein (CBP)" and any variants not specifically listed, may be used herein interchangeably, and as used throughout the present application and claims refer to proteinaceous material including single or multiple proteins, and extends to those proteins having the amino acid sequence data described herein and identified by SEQ ID NO:2, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the term "choline binding protein (CBP)" is intended to include within its scope proteins specifically recited herein as well as all substantially homologous analogs and allelic variations.

This invention provides an isolated immunogenic polypeptide comprising an amino acid sequence of a choline binding protein CbpG. It is contemplated by this invention that the immunogenic polypeptide has the amino acid sequence set forth in SEQ ID NO:2, including fragments, mutants, variants, analogs, or derivatives, thereof This invention is directed to analogs of the polypeptide which comprise the amino acid sequence as set forth above. The analog polypeptide may have an N-terminal methionine or a polyhistidine optionally attached to the N or COOH terminus of the polypeptide which comprise the amino acid sequence.

In another embodiment, this invention contemplates peptide fragments of the polypeptide which result from proteolytic digestion products of the polypeptide. In another embodiment, the derivative of the polypeptide has one or more chemical moieties attached thereto. In another embodiment the chemical moiety is a water soluble polymer. In another embodiment the chemical moiety is polyethylene glycol. In another embodiment the chemical moiety is mon-, di-, tri- or tetrapegylated. In another embodiment the chemical moiety is N-terminal monopegylated.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicty and antigenicity of heterologous compounds. For example, a PEG adduct of a human protein might be useful for the treatment of disease in other mammalian species without the risk of triggering a severe immune response. The compound of the present invention may be delivered in a microencapsulation device so as to reduce or prevent an host immune response against the compound or against cells which may produce the compound. The compound of the present invention may also be delivered microencapsulated in a membrane, such as a liposome.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

In one embodiment, the amino acid residues of the polypeptide described herein are preferred to be in the "L" isomeric form. In another embodiment, the residues in the "D" isomeric form can be substituted for any L-amino acid residue, as long as the desired functional property of lectin activity is retained by the polypeptide. $NH_2$ refers to the free amino group present at the amino terminus of a polypeptide. COOH refers to the free carboxy group present at the carboxy terminus of a polypeptide. Abbreviations used herein are in keeping with standard polypeptide nomenclature, J. Biol. Chem., 243:3552–59 (1969).

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

Synthetic polypeptide, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile $N^\alpha$-amino protected 9-fluorenylmethoxycarbonyl (Fmoc) amino acids first described by Carpino and Han (1972, J. Org. Chem. 37:3403–3409). Thus, polypeptide of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated. In one aspect of the invention, the peptides may comprise a special amino acid at the C-terminus which incorporates either a $CO_2H$ or $CONH_2$ side chain to simulate a free glycine or a glycine-amide group. Another way to consider this special residue would be as a D or L amino acid analog with a side chain consisting of the linker or bond to the bead. In one embodiment, the pseudo-free C-terminal residue may be of the D or the L optical configuration; in another embodiment, a racemic mixture of D and L-isomers may be used.

In an additional embodiment, pyroglutamate may be included as the N-terminal residue of the peptide. Although pyroglutamate is not amenable to sequence by Edman degradation, by limiting substitution to only 50% of the peptides on a given bead with N-terminal pyroglutamate, there will remain enough non-pyroglutamate peptide on the bead for sequencing. One of ordinary skill would readily recognize that this technique could be used for sequencing of any peptide that incorporates a residue resistant to Edman degradation at the N-terminus. Other methods to characterize individual peptides that demonstrate desired activity are described in detail infra. Specific activity of a peptide that comprises a blocked N-terminal group, e.g., pyroglutamate, when the particular N-terminal group is present in 50% of the peptides, would readily be demonstrated by comparing activity of a completely (100%) blocked peptide with a non-blocked (0%) peptide.

In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189–199; Hruby et al., 1990, Biochem J. 268:249–262); the present invention provides a method to produce a constrained peptide that incorporates random sequences at all other positions.

A constrained, cyclic or rigidized peptide may be prepared synthetically, provided that in at least two positions in the sequence of the peptide an amino acid or amino acid analog is inserted that provides a chemical functional group capable of cross-linking to constrain, cyclise or rigidize the peptide after treatment to form the cross-link. Cyclization will be favored when a turn-inducing amino acid is incorporated. Examples of amino acids capable of cross-linking a peptide are cysteine to form disulfide, aspartic acid to form a lactone or a lactase, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson (1980, Biophys. Biochem. Res. Commun. 94:1128–1132). A peptide in which the peptide sequence comprises at least two amino acids capable of cross-linking may be treated, e.g., by oxidation of cysteine residues to form a disulfide or addition of a metal ion to form a chelate, so as to cross-link the peptide and form a constrained, cyclic or rigidized peptide.

The present invention provides strategies to systematically prepare cross-links. For example, if four cysteine residues are incorporated in the peptide sequence, different protecting groups may be used (Hiskey, 1981, in The Peptides: Analysis, Synthesis, Biolog, Vol. 3, Gross and Meienhofer, eds., Academic Press: New York, pp. 137–167; Ponsanti et al., 1990, Tetrahedron 46:8255–8266). The first pair of cysteine may be deprotected and oxidized, then the second set may be deprotected and oxidized. In this way a defined set of disulfide cross-links may be formed. Alternatively, a pair of cysteine and a pair of collating amino acid analogs may be incorporated so that the cross-links are of a different chemical nature.

The following non-classical amino acids may be incorporated in the peptide in order to introduce particular conformational motifs: 1,2,3,4-tetrahydroisoquinoline-3-carboxylate (Kazmierski et al., 1991, J. Am. Chem. Soc. 113:2275–2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53–76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al., 1985, J. Org. Chem. 50:5834–5838); β-sheet inducing analogs (Kemp et al., 1988, Tetrahedron Lett. 29:5081–5082); β-turn inducing analogs (Kemp et al., 1988, Tetrahedron Lett. 29:5057–5060); -helix inducing analogs (Kemp et al., 1988, Tetrahedron Lett. 29:4935–4938); γ-turn inducing analogs (Kemp et al., 1989, J. Org. Chem. 54:109:115); and analogs provided by the following references: Nagai and Sato, 1985, Tetrahedron Lett. 26:647–650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853–3856); tretrazol (Zabrocki et al., 1988, J. Am. Chem. Soc. 110:5875–5880); DTC (Samanen et al., 1990, Int. J. Protein Pep. Res. 35:501:509); and analogs taught in Olson et al., 1990, J. Am. Chem. Sci. 112:323–333 and Garvey et al., 1990, J. Org. Chem. 56:436. Conformationally restricted mimetics of beta turns and beta bulges, and peptides containing them, are described in U.S. Pat. No. 5,440,013, issued Aug. 8, 1995 to Kahn.

The present invention further provides for modification or derivatization of the polypeptide or peptide of the invention. Modifications of peptides are well known to one of ordinary skill, and include phosphorylation, carboxymethylation, and acylation. Modifications may be effected by chemical or enzymatic means. In another aspect, glycosylated or fatty acylated peptide derivatives may be prepared. Preparation of glycosylated or fatty acylated peptides is well known in the art. Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure —$(CH_2)_n CH_3$ may be incorporated in the peptide. This and other peptide-fatty acid conjugates suitable for use in the present invention are disclosed in U.K. Patent GB-8809 162.4, International Patent Application PCT/AU89/00166, and reference 5, supra.

Mutations can be made in a nucleic acid encoding the polypeptide such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Synthetic DNA sequences allow convenient construction of genes which will express analogs or "muteins". A general method for site-specific incorporation of unnatural amino acids into proteins is described in Noren, et al. *Science,* 244:182–188 (April 1989). This method may be used to create analogs with unnatural amino acids.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

In an additional embodiment, pyroglutamate may be included as the N-terminal residue of the peptide. Although pyroglutamate is not amenable to sequence by Edman degradation, by limiting substitution to only 50% of the peptides on a given bead with N-terminal pyroglutatamate, there will remain enough non-pyroglutamate peptide on the bead for sequencing. One of ordinary skill in would readily recognize that this technique could be used for sequencing of any peptide that incorporates a residue resistant to Edman degradation at the N-terminus. Other methods to characterize individual peptides that demonstrate desired activity are described in detail infra. Specific activity of a peptide that comprises a blocked N-terminal group, e.g., pyroglutamate, when the particular N-terminal group is present in 50% of the peptides, would readily be demonstrated by comparing activity of a completely (100%) blocked peptide with a non-blocked (0%) peptide.

Chemical Moieties For Derivatization. Chemical moieties suitable for derivatization may be selected from among water soluble polymers. The polymer selected should be water soluble so that the component to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For the present component or components, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co- polymers, polyoxyethylated polyols and polyvinyl alcohol. Polyethylene glycol propionaldenhyde may have advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached may vary, and one skilled in the art will be able to ascertain the effect on function. One may mono-derivative, or may provide for a di-, tri-, tetra- or some combination of derivatization, with the same or different chemical moieties (e.g., polymers, such as different weights of polyethylene glycols). The proportion of polymer molecules to component or components molecules will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the component or components with consideration of effects on functional or antigenic domains of the protein. There are a number of attachment methods available to those skilled in the art, e.g., EP 0 401 384 herein incorporated by reference (coupling PEG to G-CSF), see also Malik etal., 1992, *Exp. Hematol.* 20:1028–1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group include lysine residues and the—terminal amino acid residues; those having a free carboxyl group include aspartic acid residues glutamic acid residues and the C-terminal amino acid residue. Sulfhydrl groups may also be used as a reactive group for attaching the polyethylene glycol molecule(s). Preferred for therapeutic purposes is attachment at an amino group, such as attachment at the N-terminus or lysine group.

This invention provides an isolated nucleic acid encoding a polypeptide comprising an amino acid sequence of a choline binding protein CbpG. This invention provides an isolated nucleic acid encoding a polypeptide comprising an amino acid sequence of a choline binding protein selected from the group of choline binding proteins CbpG as set forth in FIG. 2. In one embodiment the nucleic acid is set forth SEQ ID NO:3, including fragments, mutants, variants, analogs, or derivatives, thereof. The nucleic acid is DNA, cDNA, genomic DNA, RNA. Further, the isolated nucleic acid may be operatively linked to a promoter of RNA transcription. It is contemplated that the nucleic acid is used to competitively inhibit the lectin activity.

This invention further provides an isolated nucleic acid encoding an N-terminal CbpG truncate. In one embodiment the nucleic acid encodes an N-terminal CbpG truncate comprising amino acids 1–90 of CbpG. In a further embodiment, the nucleic acid encoding an N-terminal CbpG truncate comprising less than amino acids 1–90 of CbpG. In a particular embodiment the nucleic acid is set forth in SEQ ID NO:12, including fragments, mutants, variants, analogs or derivatives thereof.

A "vector" is a replicon, such as plasmid, phage or cosmid, to which another DNA segment may be attached so as to bring about the replication of the attached segment.

A "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

Further this invention also provides a vector which comprises the above-described nucleic acid molecule. The promoter may be, or is identical to, a bacterial, yeast, insect or mammalian promoter. Further, the vector may be a plasmid, cosmid, yeast artificial chromosome (YAC), bacteriophage or eukaryotic viral DNA.

Other numerous vector backbones known in the art as useful for expressing protein may be employed. Such vectors include, but are not limited to: adenovirus, simian virus 40 (SV40), cytomegalovirus (CMV), mouse mammary tumor virus (MMTV), Moloney murine leukemia virus, DNA delivery systems, i.e. liposomes, and expression plasmid delivery systems. Further, one class of vectors comprises DNA elements derived from viruses such as bovine papilloma virus, polyoma virus, baculovirus, retroviruses or Semliki Forest virus. Such vectors may be obtained commercially or assembled from the sequences described by methods well-known in the art.

This invention also provides a host vector system for the production of a polypeptide which comprises the vector of a suitable host cell. Suitable host cells include, but are not limited to, prokaryotic or eukaryotic cells, e.g. bacterial cells (including gram positive cells), yeast cells, fungal cells, insect cells, and animal cells. Numerous mammalian cells may be used as hosts, including, but not limited to, the mouse fibroblast cell NIH 3T3, CHO cells, HeLa cells, Ltk- cells, Cos cells, etc.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., $E.$ $coli$ plasmids col E1, pCR1, pBR322, pMB9 and their derivatives, plasmids such as RP4; phage DNAS, e.g., the numerous derivatives of phage $\lambda$, e.g., NM989, and other phage DNA, e.g., M13 and filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences— sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage $\lambda$, the control regions of fd coat protein, the promoter for 3-phosphoglycerate kinase or other glycolytic enzymes, the promoters of acid phosphatase (e.g., Pho5), the promoters of the yeast $\alpha$-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of $E.$ $coli$, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

This invention further provides a method of producing a polypeptide which comprises growing the above-described host vector system under suitable conditions permitting the production of the polypeptide and recovering the polypeptide so produced.

This invention further provides an antibody capable of specifically recognizing or binding to the isolated polypeptide. The antibody may be a monoclonal or polyclonal antibody. Further, the antibody may be labeled with a detectable marker that is either a radioactive, calorimetric, fluorescent, or a luminescent marker. The labeled antibody may be a polyclonal or monoclonal antibody. In one embodiment, the labeled antibody is a purified labeled antibody. Methods of labeling antibodies are well known in the art.

The term "antibody" includes, by way of example, both naturally occurring and non-naturally occurring antibodies. Specifically, the term "antibody" includes polyclonal and monoclonal antibodies, and fragments thereof Furthermore, the term "antibody" includes chimeric antibodies and wholly synthetic antibodies, and fragments thereof Such antibodies include but are not limited to polyclonal, monoclonal, chimeric, single chain, Fab fragments, and an Fab expression library.

Various procedures known in the art may be used for the production of polyclonal antibodies to polypeptide or derivatives or analogs thereof (see, e.g., Antibodies—A Laboratory Manual, Harlow and Lane, eds., Cold Spring Harbor Laboratory Press: Cold Spring Harbor, N.Y., 1988). For the production of antibody, various host animals can be immunized by injection with the choline binding polypeptide CbpG, an immunogenic fragment thereof, or a derivative (e.g., fragment or fusion protein) thereof, including but not limited to rabbits, mice, rats, sheep, goats, etc. In one embodiment, the polypeptide can be conjugated to an immunogenic carrier, e.g., bovine serum albumin (BSA) or keyhole limpet hemocyanin (KLH). Various adjuvant may be used to increase the immunological response, depending on the host species.

For preparation of monoclonal antibodies, or fragment, analog, or derivative thereof, any technique that provides for the production of antibody molecules by continuous cell lines in culture may be used (see, e.g., Antibodies—A Laboratory Manual, Harlow and Lane, eds., Cold Spring Harbor Laboratory Press: Cold Spring Harbor, N.Y., 1988). These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in Monoclonal Antibodies and Cancer Therapy, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for a polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves. An additional embodiment of the invention utilizes the techniques described for the construction of Fab expression libraries (Huse et al., 1989, Science 246:1275–1281) to allow rapid and easy identification of monoclonal Fab fragments with the desired specificity for the polypeptide, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g, with radioisotopes (preferably technetium or iodine); magnetic resonance shift reagents (such as gadolinium and manganese); or radio-opaque reagents.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, aurarnine, Texas Red, AMCA blue and Lucifer Yellow. A particular detecting material is anti-rabbit antibody prepared in goats and conjugated with fluorescein through an isothiocyanate. The polypeptide can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U. S. Pat. Nos. 3,654,090; 3,850,752; and 4,016,043 are referred to by way of example for their disclosure of alternate labeling material and methods.

Diagnostic Applications

In a further embodiment of this invention, commercial test kits suitable for use by a medical specialist may be prepared to determine the presence or absence of predetermined binding activity or predetermined binding activity capability to suspected target cells. In accordance with the testing techniques discussed above, one class of such kits will contain at least the labeled polypeptide or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined bacterial binding activity, comprising:

(a) a predetermined amount of at least one labeled immunochemically reactive component obtained by the direct or indirect attachment of the present polypeptide or a specific binding partner thereto, to a detectable label;

(b) other reagents; and (c) directions for use of said kit.

Therapeutic Applications

The therapeutic possibilities that are raised by the existence of the choline binding protein CbpG derive from the fact that the choline binding protein of the present invention is involved in or required for pneumococcal colonization and attachment, critical for bacterial survival and virulence in the human host.

Thus, a mutation in such choline binding protein CbpG leads to the inability to adhere to the host cells and the failure to colonize in said host. In a further aspect, an N-terminal CbpG truncate, acts as an immunotherapeutic fragment which binds to the cell target but prevents adhesion of the bacteria, particularly Streptococcus. In a particular embodiment, the N-terminal CbpG truncate comprises the amino acid sequence as set forth in SEQ ID NO:11. In a further embodiment, the N-terminal CbpG truncate consists of amino acids 1–90 of the CbpG choline binding protein. In a still further embodiment, the N-terminal CbpG truncate is a truncate of less than amino acids 1–90 of CbpG.

As suggested earlier and elaborated further on herein, the present invention contemplates therapeutic intervention in the cascade of reactions, specifically colonization and attachment, in which the choline binding protein CbpG is implicated, to thereby block or reduce the virulence of bacteria, particularly Streptococcus, most particularly pneumococcus.

Modulators of Choline Binding Protein

Thus, in instances where it is desired to reduce or inhibit the effects resulting from the choline binding protein CbpG of the present invention, an appropriate inhibitor of the choline binding protein CbpG could be introduced to block the activity of the choline binding protein CbpG.

The present invention contemplates screens for a modulator of the choline binding protein CbpG, in particular, directly or indirectly through the choline binding site. The present invention further contemplates screens for a modulator of the choline binding protein CbpG, in particular, directly or indirectly through the N-terminal activity domain. In one such embodiment, an expression vector containing the choline binding protein CbpG of the present invention, or a derivative or analog thereof, is placed into a cell in the presence of at least one agent suspected of exhibiting choline binding protein CbpG modulator activity. The cell is preferably a bacterial cell and most preferably a pneumococcal cell. The amount of adhesion or binding activity is determined and any such agent is identified as a modulator when the amount of adhesion or binding activity in the presence of such agent is different than in its absence. The vectors may be introduced by any of the methods described above.

In a related embodiment the choline binding protein CbpG is expressed and the step of determining the amount of adhesion or binding activity is performed by determining the amount of binding to nasopharyngeal cells in vitro. In a further embodiment an N-terminal choline binding protein truncate of the choline binding protein CbpG is expressed and the step of determining the amount of adhesion or binding activity is performed by determining the amount of binding to nasopharyngeal cells in vitro.

When the amount of adhesion or binding activity in the presence of the modulator is greater than in its absence, the modulator is identified as an agonist or activator of the choline binding protein CbpG, whereas when the amount of adhesion binding activity in the presence of the modulator is less than in its absence, the modulator is identified as an antagonist or inhibitor of the choline binding protein CbpG. As any person having skill in the art would recognize, such determinations as these and those below could require some form of statistical analysis, which is well within the skill in the art.

Natural effectors found in cells expressing choline binding protein CbpG can be fractionated and tested using standard effector assays as exemplified herein, for example. Thus an agent that is identified can be a naturally occurring adhesion or binding modulator. Alternatively, natural products libraries can be screened using the assays of the present invention for screening such agents.

Another approach uses recombinant bacteriophage to produce large libraries. Using the "phage method" [Scott and Smith, 1990, Science 249:386–390 (1990); Cwirla, et al., Proc. Natl. Acad. Sci., 87:6378–6382 (1990); Devlin et al., Science, 249:404–406 (1990)], very large libraries can be constructed ($10^6$–$10^8$ chemical entities). Yet another approach uses primarily chemical methods, of which the Geysen method [Geysen et al., Molecular Immunology 23:709–715 (1986); Geysen et al. J. Immunologic Method 102:259–274 (1987)] and the method of Fodor et al. [Science 251:767–773 (1991)] are examples. Furka et al. [14th International Congress of Biochemistry, Volume 5, Abstract FR:013 (1988); Furka, Int. J. Peptide Protein Res. 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested.

In another aspect, synthetic libraries [Needels et al., Proc. Natl. Acad. Sci. USA 90:10700–4 (1993); Ohlmeyer et al.,

*Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for such an agent.

This invention provides antagonist or blocking agents which include but are not limited to: peptide fragments, mimetic, a nucleic acid molecule, a ribozyme, a polypeptide, a small molecule, a carbohydrate molecule, a monosaccharide, an oligosaccharide or an antibody. Also, agents which competitively block or inhibit pneumococcal bacterium are contemplated by this invention. This invention provides an agent which comprises an inorganic compound, a nucleic acid molecule, an oligonucleotide, an organic compound, a peptide, a peptidomimetic compound, or a protein which inhibits the polypeptide.

Vaccines

This invention provides a vaccine which comprises a polypeptide bacterial choline binding protein CbpG and a pharmaceutically acceptable adjuvant or carrier. This invention provides a vaccine which comprises a combination of at least two polypeptide bacterial choline binding proteins comprising CbpG and at least one other choline binding protein and a pharmaceutically acceptable adjuvant or carrier. The polypeptide may comprise an amino acid sequence of a choline binding protein CbpG as set forth in FIG. 2 and SEQ ID NO:2.

The polypeptide may comprise an N-terminal truncate of a choline binding protein CbpG. In a particular embodiment, the N-terminal CbpG truncate comprises the amino acid sequence set forth in SEQ ID NO:11. In a further embodiment, the N-terminal CbpG truncate consists of amino acids 1–90 of the CbpG choline binding protein. Still further, the N-terminal truncate may comprise less than amino acids 1–90 of CbpG.

This invention further provides a vaccine comprising an isolated nucleic acid encoding a bacterial choline binding protein CbpG and a pharmaceutically acceptable adjuvant or carrier. This invention further provides a vaccine comprising isolated nucleic acid encoding a combination of at least two polypeptide bacterial choline binding proteins comprising CbpG and at least one other choline binding protein and a pharmaceutically acceptable adjuvant or carrier. This invention still further provides a vaccine comprising an isolated nucleic acid encoding a N-terminal truncate of choline binding protein CbpG and a pharmaceutically acceptable adjuvant or carrier. The nucleic acid may comprise a nucleic acid sequence of a choline binding protein CbpG as set forth in FIG. 2 and SEQ ID NO:3.

Active immunity against Gram positive bacteria, particularly pneumococcus, can be induced by immunization (vaccination) with an immunogenic amount of the polypeptide, or peptide derivative or immunogenic fragment thereof or N-terminal truncate thereof, and an adjuvant, wherein the polypeptide, or antigenic derivative or; fragment thereof, is the antigenic component of the vaccine. The polypeptide, or antigenic derivative or fragment thereof, may be one antigenic component, in the presence of other antigenic components in a vaccine. For instance, the polypeptide of the present invention or immunogenic fragment thereof may be combined with other known pneumococcal polypeptides, or immunogenic fragments thereof or N-terminal truncates thereof, as for instance other choline binding protein(s), including for instance CbpA, LytA, and/ or PspA in a multi-component vaccine. In addition, the polypeptide of the present invention or immunogenic fragments thereof may be combined with bacterial zinc metalloprotease, ZmpB or immunogenic fragments thereof. Such multi-component vaccine may be utilized to enhance immune response, even in cases where the polypeptide of the present invention elicits a response on its own. The polypeptide of the present invention may also be combined with existing vaccines, whole bacterial or capsule-based vaccines, alone or in combination with other choline binding proteins or ZmpB, to enhance such existing vaccines.

The invention further provides a vaccine which comprises a non-adherent, non-virulent mutant, including but not limited to the cbpG mutants herein described. Medaglini et al (Madaglini et al (1995) *Proc Natl Acad Sci USA* 92;6868–6872) and Oggioni and Pozzi (Oggioni, M. R. and Pozzi, G. (1996) *Gene* 169:85–90) have previously described the use of *Streptococcus gordonii*, a commensal bacterium of the human oral cavity, as live vaccine delivery vehicles and for heterologous gene expression. Such cbpG mutant can therefore be utilized as a vehicle for expression of immunogenic proteins for the purposes of eliciting an immune response to such other proteins in the context of vaccines. Active immunity against Gram positive bacteria, particularly pneumococcus, can be induced by immunization (vaccination) with an immunogenic amount of the cbpG vehicle expressing an immunogenic protein. Also contemplated by the present invention is the use of any such cbpG mutant in expressing a therapeutic protein in the host in the context of other forms of therapy.

The polypeptide of the present invention, or fragments thereof, can be prepared in an admixture with an adjuvant to prepare a vaccine. Preferably, the polypeptide or peptide derivative or fragment thereof, used as the antigenic component of the vaccine is an antigen common to all or many strains of a species of Gram positive bacteria, or common to closely related species of bacteria, for instance Streptococcus.

Vectors containing the nucleic acid-based vaccine of the invention can be introduced into the desired host by methods known in the art, e.g., transfection, electroporation, micro injection, transduction, cell fusion, DEAE dextran, calcium phosphate precipitation, lipofection (lysosome fusion), use of a gene gun, or a DNA vector transporter (see, e.g., Wu et al., 1992, *J. Biol. Chem.* 267:963–967; Wu and Wu, 1988, *J. Biol. Chem.* 263:14621–14624; Hartmut et al., Canadian Patent Application No. 2,012,311, filed Mar. 15, 1990).

The vaccine can be administered via any parenteral route, including but not limited to intramuscular, intraperitoneal, intravenous, and the like. Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen, is desirable. Since immune cells are continually replicating, they are ideal target for retroviral vector-based nucleic acid vaccines, since retroviruses require replicating cells.

Passive immunity can be conferred to an animal subject suspected of suffering an infection with a Gram positive bacterium, preferably streptococcal, and more preferably pneumoccal, by administering antiserum, polyclonal antibodies, or a neutralizing monoclonal antibody against a polypeptide of the invention to the subject. A combination of antibodies can be, for instance, directed against at least two polypeptide bacterial choline binding proteins comprising CbpG and at least one other choline binding protein.

Although passive immunity does not confer long term protection, it can be a valuable tool for the treatment of a bacterial infection in a subject who has not been vaccinated. Passive immunity is particularly important for the treatment of antibiotic resistant strains of Gram positive bacteria, since no other therapy may be available. Preferably, the antibodies administered for passive immune therapy are autologous antibodies. For example, if the subject is a human, preferably the antibodies are of human origin or have been "humanized," in order to minimize the possibility of an immune response against the antibodies. The active or passive vaccines of the invention can be used to protect an animal subject from infection of a Gram positive bacteria, preferably streptococcus, and more preferably, pneumococcus.

This invention provides a method for treating a subject infected with or exposed to pneumococcal bacterium comprising administering to the subject a therapeutically effective amount of the vaccine, thereby treating the subject.

Pharmaceutical Compositions

This invention provides a pharmaceutical composition comprising an amount of the polypeptide as described and a pharmaceutically acceptable carrier or diluent. This invention provides a pharmaceutical composition comprising an amount of a choline binding protein CbpG and a pharmaceutically acceptable carrier or diluent. This invention provides a pharmaceutical composition comprising an amount of at least two choline binding proteins comprising CbpG and at least one other choline binding protein and a pharmaceutically acceptable carrier or diluent. The invention further provides a pharmaceutical composition comprising an amount of the polypeptide of SEQ ID NO:2, including fragments, mutants, variants, analogs or derivatives thereof, and a pharmaceutically acceptable carrier or diluent. This invention still further provides a pharmaceutical composition comprising an amount of an N-terminal truncate of a choline binding protein CbpG. In a particular embodiment, the N-terminal CbpG truncate comprises amino acids 1–90 of CbpG, as set out in SEQ ID NO:11, or active fragments, mutants, variants, analogs or derivatives thereof.

For example, such pharmaceutical composition for preventing pneumococcal attachment to mucosal surface may include antibody to choline binding protein CbpG or any combination of anti-CbpG antibody and at least one other antibody directed against another choline binding protein. Blocking adherence using such antibody blocks the initial step in infection thereby reducing colonization. This in turn decreases person to person transmission and prevents development of symptomatic disease. A further example of a pharmaceutical composition for preventing pneumococcal attachment may include an N-terminal CbpG truncaate. In a particular embodiment, such N-terminal truncate comprises the amino acid set out in SEQ ID NO:11, or active fragments thereof This invention provides a method of inducing an immune response in a subject which has been exposed to or infected with a pneumococcal bacterium comprising administering to the subject an amount of the pharmaceutical composition, thereby inducing an immune response.

This invention provides a method for preventing infection by a pneumococcal bacterium in a subject comprising administering to the subject an amount of the pharmaceutical composition effective to block activity of the choline binding protein CbpG, thereby preventing pneumococcal bacterium attachment, and further preventing infection by a pneumococcal bacterium.

This invention provides a method for preventing infection by a pneumococcal bacterium in a subject comprising administering to the subject an amount of a pharmaceutical composition comprising the antibody and a pharmaceutically acceptable carrier or diluent, thereby preventing infection by a pneumococcal bacterium.

This invention provides a method of inhibiting colonization of host cells in a subject which has been exposed to or infected with a pneumococcal bacterium comprising administering to the subject an amount of the pharmaceutical composition comprising the polypeptide consisting of the amino acid sequence as set forth in SEQ ID NO:2, or SEQ ID NO:11, or immunogenic fragments thereof thereby inducing an immune response. The therapeutic peptide that blocks colonization is delivered via the respiratory mucosa. The pharmaceutical composition comprises the polypeptide consisting of the amino acid sequence as set forth in SEQ ID NO:2 or SEQ ID NO:11.

As used herein, "pharmaceutical composition" could mean therapeutically effective amounts of polypeptide products of the invention together with suitable diluents, preservatives, solubilizers, emulsifiers, adjuvant and/or carriers useful in therapy against bacterial infection or in inducing an immune response. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of choline binding protein CbpG and the polypeptides of the present invention. The choice of compositions will depend on the physical and chemical properties of the polypeptide. Controlled or sustained release compositions include formulation in lipophilic depots (e.g., fatty acids, waxes, oils). Also comprehended by the invention are particulate compositions coated with polymers (e.g., poloxamers or poloxamines) and the polypeptides of the present invention coupled to antibodies directed against tissue-specific receptors, ligands or antigens or coupled to ligands of tissue-specific receptors. Other embodiments of the compositions of the invention incorporate particulate forms, protective coatings, protease inhibitors or permeation enhancers for various routes of administration, including parenteral, pulmonary, nasal and oral.

Further, as used herein "pharmaceutically acceptable carrier" are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.,* 1984, Benjamin/Cummings: Menlo Park, Calif., p. 384). Often, a primary challenge with an antigen alone, in the absence of an adjuvant, will fail to elicit a humoral or cellular immune response. Adjuvant include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (*bacille Calmette-Guerin*) and *Corynebacterium parvum*. Preferably, the adjuvant is pharmaceutically acceptable.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from mucosal surfaces or the circulation and may therefore elicit relatively short-lived pharmacological activity. Consequently, frequent administrations of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Dosages. The sufficient amount may include but is not limited to from about 1 μg/kg to about 1000 mg/kg. The amount may be 10 mg/kg. The pharmaceutically acceptable form of the composition includes a pharmaceutically acceptable carrier.

As noted above, the present invention provides therapeutic compositions comprising pharmaceutical compositions comprising vectors, vaccines, polypeptides or fragments thereof, nucleic acids and antibodies, anti-antibodies, and agents, to compete with the pneumococcus bacterium for pathogenic activities, such as adherence to host cells.

The preparation of therapeutic compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof In addition, if desired, the composition can contain minor amounts of auxiliary substances such as wetting or emulsifying agents, pH buffering agents which enhance the effectiveness of the active ingredient.

An active component can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. In the context of the present invention, a deficit in the response of the host is evidenced by continuing or spreading bacterial infection. An improvement in a clinically significant condition in the host includes a decrease in bacterial load, clearance of bacteria from colonized host cells, reduction in fever or inflammation associated with infection, or a reduction in any symptom associated with the bacterial infection.

According to the invention, the component or components of a therapeutic composition of the invention may be introduced parenterally, transmucosally, e.g., orally, nasally, pulmonarailly, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Oral or pulmonary delivery may be preferred to activate mucosal immunity; since pneumococci generally colonize the nasopharyngeal and pulmonary mucosa, mucosal immunity may be a particularly effective preventive treatment. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i e., carrier, or vehicle.

In another embodiment, the active compound can be delivered in a vesicle, in particular a liposome (see Langer, Science 249:1527–1533 (1990); Treat et al., in Liposomes in the Therapy of Infecfious Disease and Cancer, Lopez-Berestein and Fidler (eds.), Liss, New York, pp. 353–365 (1989); Lopez-Berestein, ibid., pp. 317–327; see generally ibid).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. MacromoL Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)). Preferably, a controlled release device is introduced into a subject in proximity of the site of inappropriate immune activation or a tumor. Other controlled release systems are discussed in the review by Langer (Science 249:1527–1533 (1990)).

A subject in whom administration of an active component as set forth above is an effective therapeutic regimen for a bacterial infection is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Administration with other compounds. For treatment of a bacterial infection, one may administer the present active component in conjunction with one or more pharmaceutical compositions used for treating bacterial infection, including but not limited to (1) antibiotics; (2) soluble carbohydrate inhibitors of bacterial adhesin; (3) other small molecule inhibitors of bacterial adhesin; (4) inhibitors of bacterial metabolism, transport, or transformation; (5) stimulators of bacterial lysis, or (6) anti-bacterial antibodies or vaccines directed at other bacterial antigens. Other potential active components include anti-inflammatory agents, such as steroids and non-steroidal anti-inflammatory drugs. Administration may be simultaneous (for example, administration of a mixture of the present active component and an antibiotic), or may be in seriatim.

Accordingly, in specific embodiment, the therapeutic compositions may further include an effective amount of the active component, and one or more of the following active ingredients: an antibiotic, a steroid, etc. Exemplary formulations are given below:

| Ingredient | mg/ml |
|---|---|
| Formulations | |
| Intravenous Formulation I | |
| cefotaxime | 250.0 |
| Polypeptide | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| Polypeptide | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| Polypeptide | 10.0 |
| sodium bisulfite USP | 3.2 |
| disodium edetate USP | 0.1 |
| water for injection q.s.a.d. | 1.0 ml |

-continued

| Ingredient | mg/ml |
|---|---|
| Formulations | |
| Intravenous Formulation IV | |
| Polypeptide | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation V | |
| Polypeptide antagonist | 5.0 |
| sodium bisulfite USP | 3.2 |
| disodium edetate USP | 0.1 |
| water for injection q.s.a.d. | 1.0 ml |

Thus, in a specific instance where it is desired to reduce or inhibit the infection resulting from a bacterium mediated binding of bacteria to a host cell, or an antibody thereto, or a ligand thereof or an antibody to that ligand, the polypeptide is introduced to block the interaction of the bacteria with the host cell.

Also contemplated herein is pulmonary delivery of an inhibitor of the polypeptide of the present invention having which acts as adhesin inhibitory agent (or derivatives thereof). The adhesin inhibitory agent (or derivative) is delivered to the lungs of a mammal, where it can interfere with bacterial, i.e., streptococcal, and preferably pneumococcal binding to host cells. Other reports of preparation of proteins for pulmonary delivery are found in the art [Adjei et al.(1990) *Pharmaceutical Research,* 7:565–569; Adjei et al.(1990) *International Journal of Pharmaceutics,* 63:135–144 (leuprolide acetate); Braquet et al (1989), *Journal of Cardiovascular Pharmacology,* 13(suppl. 5): 143–146 (endothelin-1); Hubbard et al.(1989) *Annals of Inernal Medicine,* Vol. III, pp. 206–212 (α1-antitrypsin); Smith et al.(1989) *J. Clin. Invest.* 84:1145–1146 (α-1-proteinase); Oswein et al., "Aerosolization of Proteins", *Proceedings of Symposium on Respiratory Drug Delivery II,* Keystone, Colo., March, (1990) (recombinant human growth hormone); Debs et al.(1988) *J. Immunol.* 140:3482–3488 (interferon-γ and tumor necrosis factor alpha); Platz et al., U.S. Pat. No. 5,284,656 (granulocyte colony stimulating factor)]. A method and composition for pulmonary delivery of drugs is described in U.S. Pat. No. 5,451,569, issued Sep. 19, 1995 to Wong et al.

All such devices require the use of formulations suitable for the dispensing of adhesin inhibitory agent (or derivative). Typically, each formulation is specific to the type of device employed and may involve the use of an appropriate propellant material, in addition to the usual diluents, adjuvant and/or carriers useful in therapy. Also, the use of liposomes, microcapsules or microspheres, inclusion complexes, or other types of carriers is contemplated. Chemically modified adhesin inhibitory agent may also be prepared in different formulations depending on the type of chemical modification or the type of device employed.

Formulations suitable for use with a nebulizer, either jet or ultrasonic, will typically comprise adhesin inhibitory agent (or derivative) dissolved in water at a concentration of about 0.1 to 25 mg of biologically active adhesin inhibitory agent per ml of solution. The formulation may also include a buffer and a simple sugar (e.g., for adhesin inhibitory agent stabilization and regulation of osmotic pressure). The nebulizer formulation may also contain a surfactant, to reduce or prevent surface induced aggregation of the adhesin inhibitory agent caused by atomization of the solution in forming the aerosol.

Formulations for use with a metered-dose inhaler device will generally comprise a finely divided powder containing the adhesin inhibitory agent (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof Suitable surfactants include sorbitan trioleate and soya lecithin. Oleic acid may also be useful as a surfactant.

The liquid aerosol formulations contain adhesin inhibitory agent and a dispersing agent in a physiologically acceptable diluent. The dry powder aerosol formulations of the present invention consist of a finely divided solid form of adhesin inhibitory agent and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of pulmonary administration of a drug are well known in the art, and manipulation of formulations, aerosolization means and construction of a delivery device require at most routine experimentation by one of ordinary skill in the art. In a particular embodiment, the mass median dynamic diameter will be 5 micrometers or less in order to ensure that the drug particles reach the lung alveoli [Wearley, L. L. (1991) *Crit. Rev. in Ther. Drug Carrier Systems* 8:333].

Systems of aerosol delivery, such as the pressurized metered dose inhaler and the dry powder inhaler are disclosed in Newman, S. P., *Aerosols and the Lung,* Clarke, S. W. and Davia, D. editors, pp. 197–22 and can be used in connection with the present invention.

In a further embodiment, as discussed in detail infra, an aerosol formulation of the present invention can include other therapeutically or pharmacologically active ingredients in addition to adhesin inhibitory agent, such as but not limited to an antibiotic, a steroid, a non-steroidal anti-inflammatory drug, etc.

Liquid Aerosol Formulations. The present invention provides aerosol formulations and dosage forms for use in treating subjects suffering from bacterial, e.g., streptococcal, in particularly pneumococcal, infection. In general such dosage forms contain adhesin inhibitory agent in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0–8.0 range, or water.

The liquid aerosol formulation of the present invention may include, as optional ingredients, pharmaceutically acceptable carriers, diluents, solubilizing or emulsifying agents, surfactants and excipients. The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

The present invention further contemplates liquid aerosol formulations comprising adhesin inhibitory agent and another therapeutically effective drug, such as an antibiotic, a steroid, a non-steroidal anti-inflammatory drug, etc.

Aerosol Dry Powder Formulations. It is also contemplated that the present aerosol formulation can be prepared as a dry powder formulation comprising a finely divided powder form of adhesin inhibitory agent and a dispersant.

Formulations for dispensing from a powder inhaler device will comprise a finely divided dry powder containing adhesin inhibitory agent (or derivative) and may also include a bulking agent, such as lactose, sorbitol, sucrose, or mannitol in amounts which facilitate dispersal of the powder from the device, e.g., 50 to 90% by weight of the formulation. The adhesin inhibitory agent (or derivative) should most advantageously be prepared in particulate form with an average particle size of less than 10 mm (or microns), most preferably 0.5 to 5 mm, for most effective delivery to the distal lung. In another embodiment, the dry powder formulation can comprise a finely divided dry powder containing adhesin inhibitory agent, a dispersing agent and also a bulking agent. Bulking agents useful in conjunction with the present formulation include such agents as lactose, sorbitol, sucrose, or mannitol, in amounts that facilitate the dispersal of the powder from the device.

The present invention further contemplates dry powder formulations comprising adhesin inhibitory agent and another therapeutically effective drug, such as an antibiotic, a steroid, a non-steroidal anti-inflammatory drug, etc.

Contemplated for use herein are oral solid dosage forms, which are described generally in *Remington's Pharmaceutical Sciences,* 18th Ed. 1990 (Mack Publishing Co. Easton PA 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the component or components (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Abducts" In: *Enzymes as Drugs*, Hocenberg and Roberts, eds., Wiley-Interscience, New York, N.Y., pp.367–383; Newmark, et al. (1982) *J. Appl. Biochem.* 4:185–189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), BPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The peptide therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextran and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the polypeptide (or derivative) are for instance the fatty acids oleic acid, linoleic acid and linolenic acid.

Pulmonary Delivery. Also contemplated herein is pulmonary delivery of the present polypeptide (or derivatives thereof). The polypeptide (or derivative) is delivered to the lungs of a mammal while inhaling and coats the mucosal surface of the alveoli. Other reports of this include Adjei et al. (1990) *Pharmaceutical Research* 7:565–569; Adjei et al. (1990) *International Journal of Pharmaceutics* 63:135–144 (leuprolide acetate); Braquet et al.(1.989) *Journal of Cardiovascular Pharmacology,* 13(suppl. 5):143–146 (endothelin-1); Hubbard etal. (1989) *Annals of Internal Medicine*, Vol. III, pp. 206–212 (a1-antitrypsin); Smith et al. (1989) *J. Clin. Invest.* 84:1145–1146 (a-1-proteinase); Oswein et al. (1990) "Aerosolization of Proteins", *Proceedings of Symposium on Respiratory Drug Delivery II*, Keystone, Colorado, March, (recombinant human growth hormone); Debs et al. (1988) *J. Immunol.* 140:3482–3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Formulations suitable for use with a nebulizer, either jet or ultrasonic, will typically comprise polypeptide (or derivative) dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the polypeptide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof Suitable surfactants include sorbitan trioleate and soya lecithin. Oleic acid may also be useful as a surfactant.

Formulations for dispensing from a powder inhaler device will comprise a finely divided dry powder containing polypeptide (or derivative) and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 mm (or microns), most preferably 0.5 to 5 mm, for most effective delivery to the distal lung.

Nasal Delivery. Nasal or nasopharyngeal delivery of the polypeptide (or derivative) is also contemplated. Nasal delivery allows the passage of the polypeptide directly over the upper respiratory tract mucosal after administering the therapeutic product to the nose, without the necessity for deposition of the product in the lung. Formulations for nasal delivery include those with dextran or cyclodextran.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLES

Identification and Characterization of Choline Binding Proteins

Figure 1:
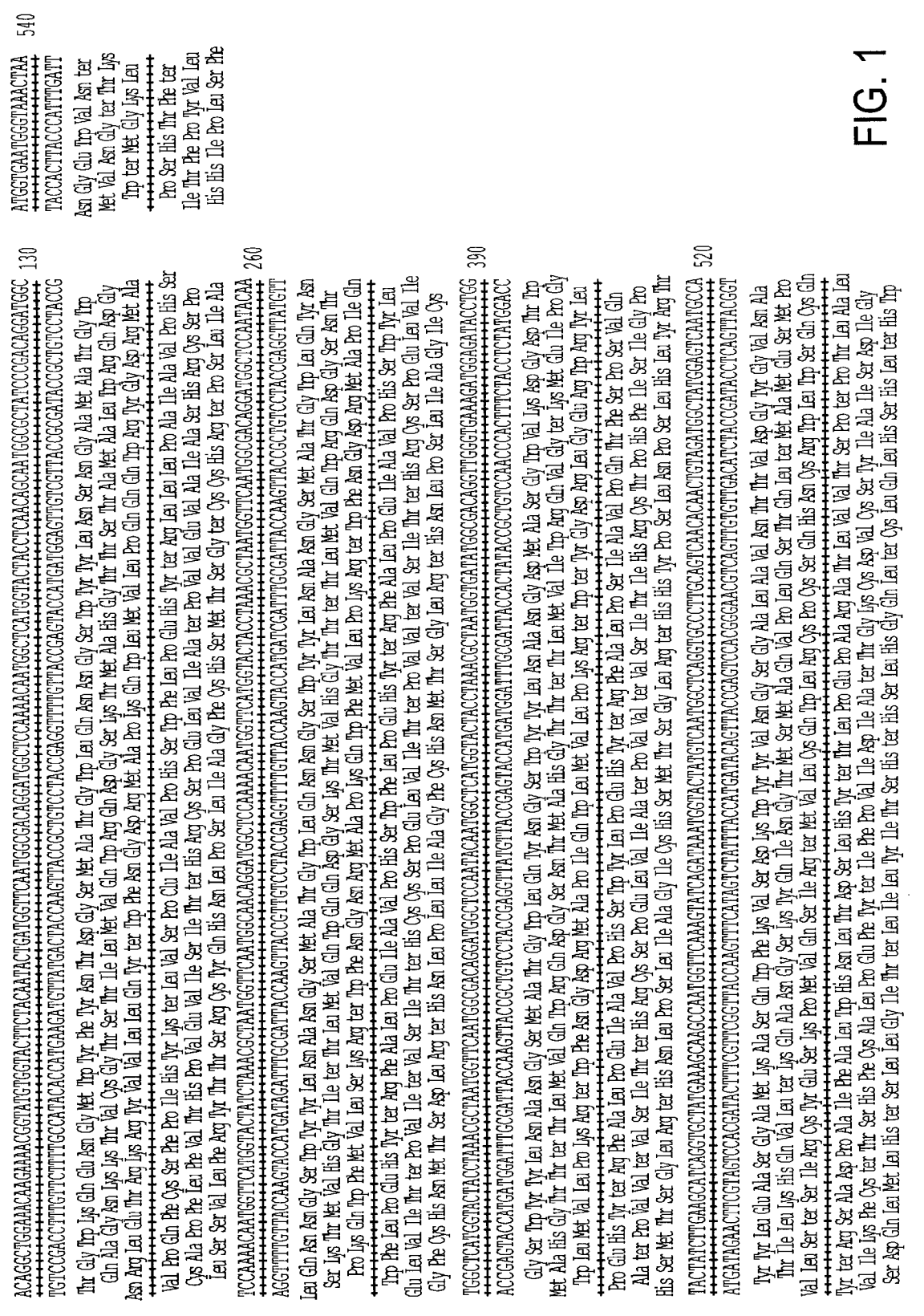

We have used the C-terminal 180 amino acids of CbpA (the choline binding domain), shown in FIG. 1 (SEQ ID NO:1) to search the pneumococcal genome to identify new members of the choline binding family of proteins. The pneumococcal database is publicly available at www.tigr.org/tdb/mdb/mdb.html and through the National Center for Biotechnology Information (at www.nih.ncbi.org). The pneumococcal database is selected and searched by the following steps: (1) select "BLAST"; (2) under "Specialized Blast Pages", select "Unfinished Microbial Genomes"; (3) then click to choose individual genomes to search; and (4) under "Eubacteria" select "*Streptococcus pneumoniae*". A search of this public database using the search engine BLAST available at www.nih.ncbi.org, with the filter and other parameters set at default, using SEQ ID NO:1 will yield the polypeptides and nucleic acids now identified in the present invention. The search identifies eight contigs which contain nine encoded choline binding polypeptides, which are unique and distinct from the recognized pneumococcal choline binding proteins PspA, LytA and CbpA, and are designated CbpB, CbpC, CbpD, CbE, CbpF, CbpG, CbpH, CbpI and CbpJ. One contig encodes two Cbps, specifically CbpF and CbpG, and required further visual analysis of the layout of the homologous choline binding domains to identify and distinguish the two unique Cbps. The amino acid and nucleic acid sequences of choline binding protein CbpG is found in FIG. 2, corresponding to SEQ ID NO:2 (amino acid) and SEQ ID NO: 3 (nucleic acid).

Characterization of CbpG

Figure 2A:
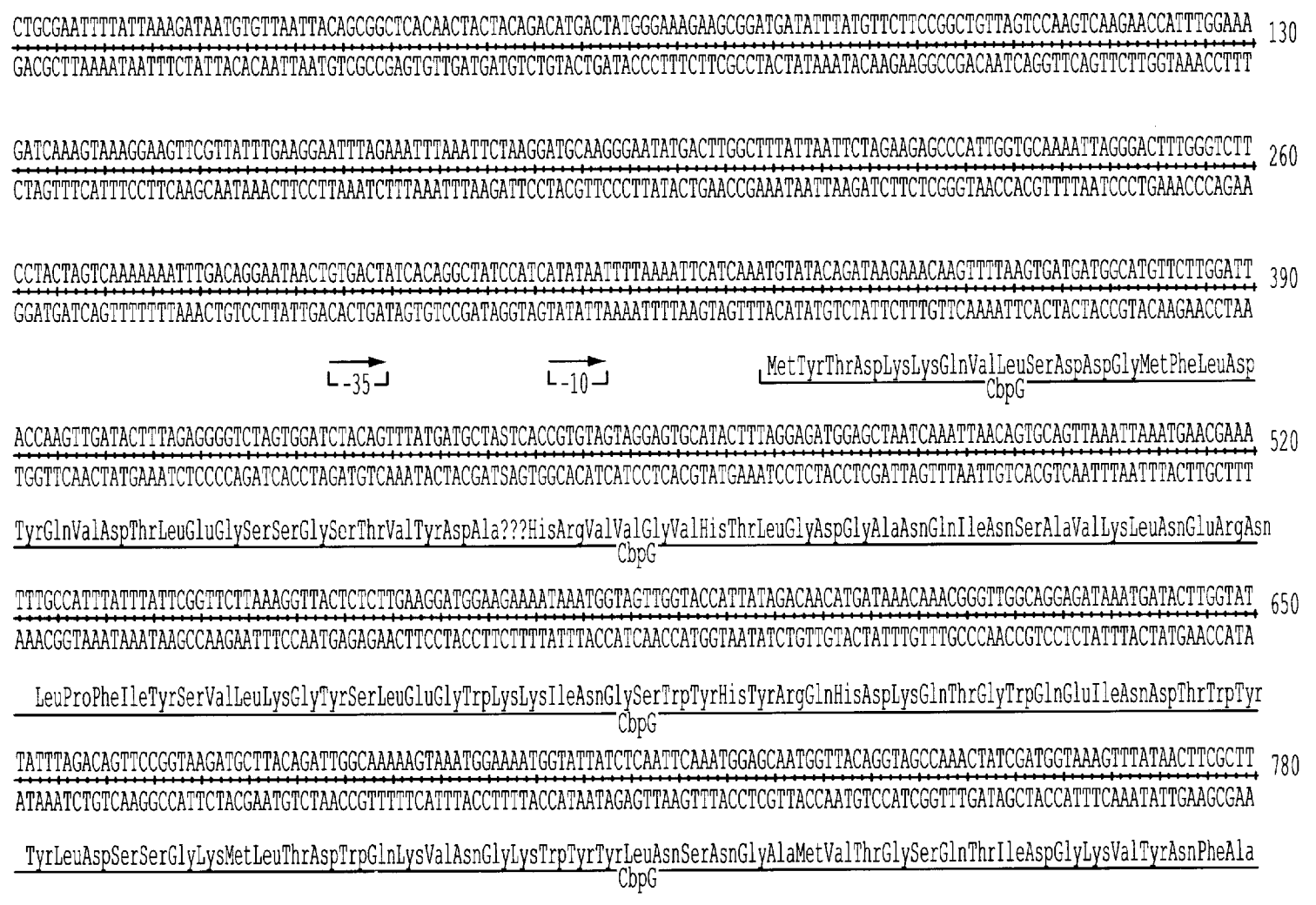
Figure 2B:
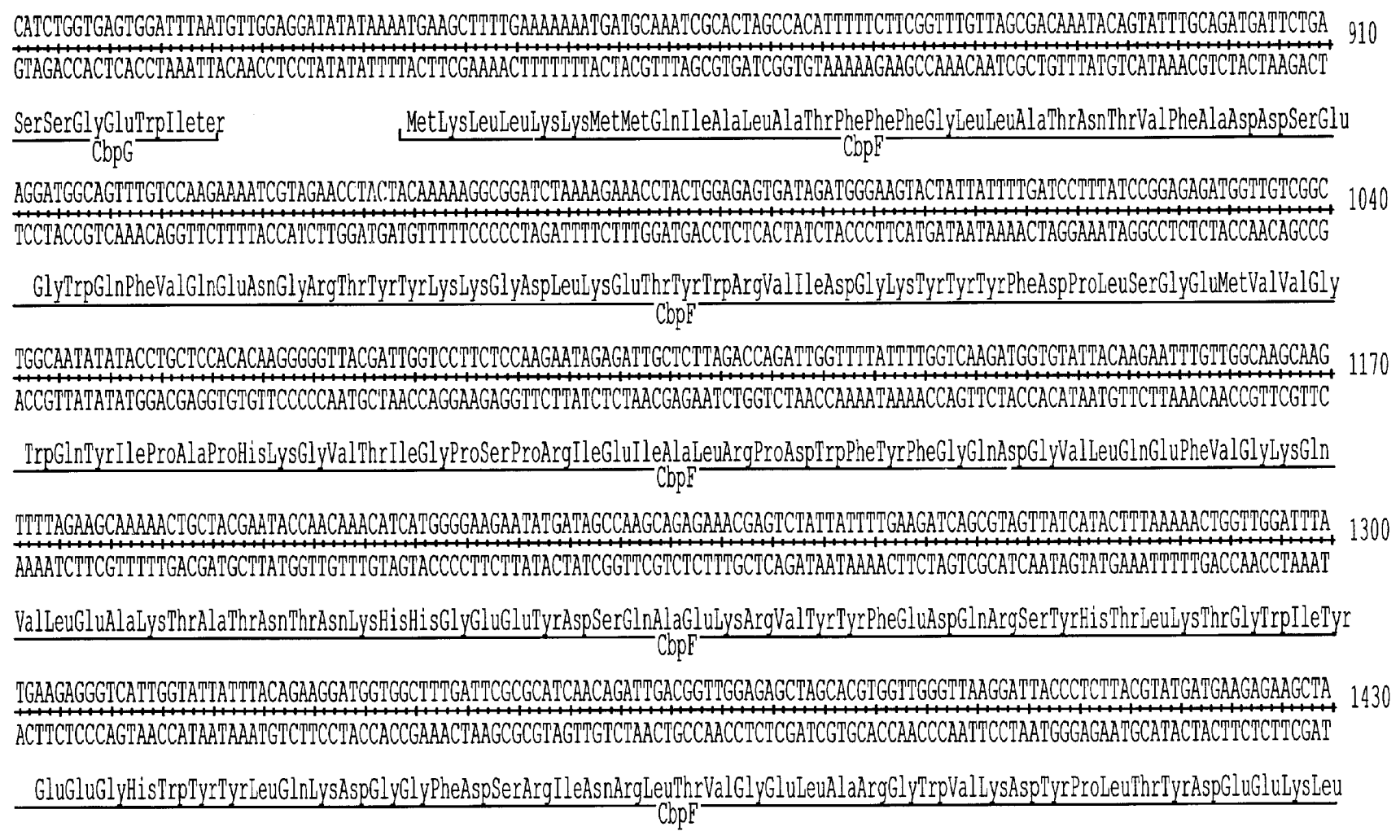
Figure 3:
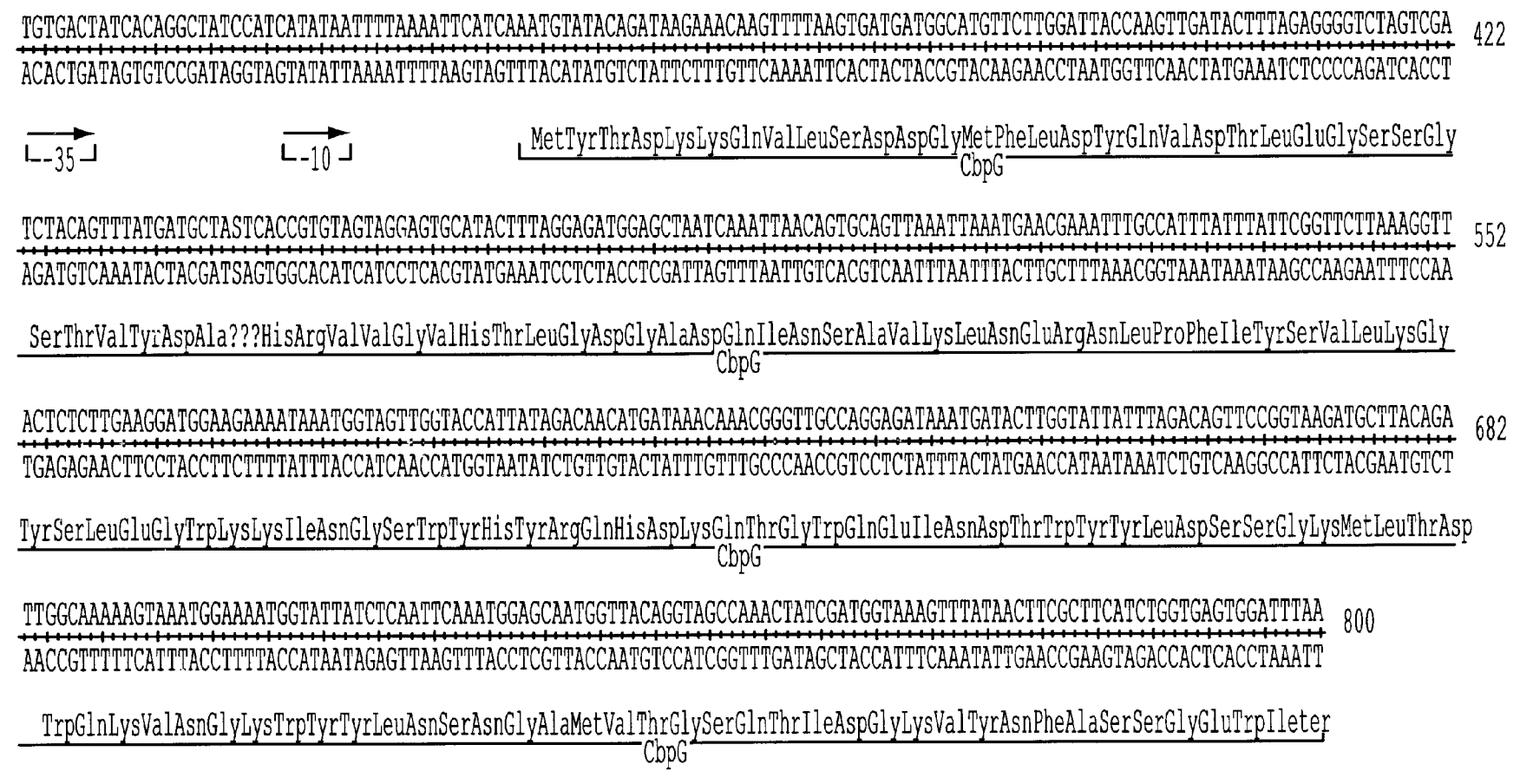

CbpG is the smallest of the choline binding proteins with an open reading frame (ORF) that is 462 nucleotides long. The CbpG gene has a 35% GC content which is consistent with the 38.5% GC content of pneumococcus. It is located upstream of the gene for CbpF and may be cotranscribed with CpbF. The DNA sequence for both CbpG and CbpF is shown in FIGS. 2A–C (SEQ ID NO:4). The amino acid sequence of the CbpG polypeptide is shown in FIG. 2 and FIG. 3 (SEQ ID NO:2). The nucleic acid sequence of CbpG including upstream promoter sequence is presented in FIG. 3 (SEQ ID NO:10). Analysis of sequences directly upstream of CbpG indicate the presence of a putative *E. coli* like promoter with a consensus –10 (TATAAT) and a –35 containing two mismatches (GTGACT). There are only 35 nucleotides between the end of the CbpG ORF and the start codon for CbpF. Sequence analysis failed to reveal a promoter in this intervening region. Therefore, CbpG and CbpF are likely cotranscribed from the promoter in front of CbpG.

The CbpG gene encodes a peptide of 154 amino acids with a predicted size of 17 kDa. The protein has two domains: (i) an N-terminal domain (amino acids 1 to 93) with a high level of homology to a 50 amino acid region of the *Enterococcus faecalis* serine proteinase and (ii) a C-terminal domain which, like all other choline binding proteins, contains the 20 amino acid repeats required for choline binding. CbpG has 2 such repeats. There were no other significant similarities to proteins in the current databases.

Functional Analysis of CbpG cbpG loss of function mutants were constructed by insertion duplication mutagenesis. An internal 220 bp fragment at the N-terminus of CbpG was amplified from Type 4 chromosomal DNA using primers 939E (5' TTC TTG aAT TcC CAA GTT GAT ACT TT (SEQ ID NO:5)) and 939B (5' ATA ATG Gat CCA ACT ACC ATT TAT TTT C (SEQ ID NO: 6)). The PCR product was digested with EcoRI and BamHI and cloned into pJDC9 and transformed into DH5 α *E.coli*. Insert was verified by size and restriction analysis and the plasmid was then transformed into *S. pneumoniae* wild type 4, selecting for erythromycin resistance. Such colonies were isolated and the position of the insert in the cbpG gene was verified by PCR.

The chpG defective mutant was then assesssed for it's ability to colonize the infant rat nasopharyx, to adhere to Detroit cells as well as to immobilized carbohydrates LNnT and sialylactose, transformation, lysis in response to detergent (DOC) and pencillin sensitivity. All of these properties have been shown to be important in pneumococcal physiology.

The ability to colonize the nasopharynx of 1 to 5 day old Sprague-Dawley rat pups was determined as described previously (Wieser J N et al (1994) *Infect Immun* 62(6): 2582–2589). For each experiment 8 to 10 rat pups were inoculated intranasally with 2.5–8×10$^3$ cfu of the cbpG-deficient mutant or the isogenic Type 4 in PBS. Colonization was assessed 48 and 96 hrs post inoculation. The results of these experiments are presented in Table 1. In four independent experiments, the cbpG defective mutant showed decreased colonization ranging from 9–35% of wild type 4. These data indicate that the cbpG-deficient mutant has an approximately 3–10 fold reduced ability to colonize the rat nasopharynx.

Figure 5:
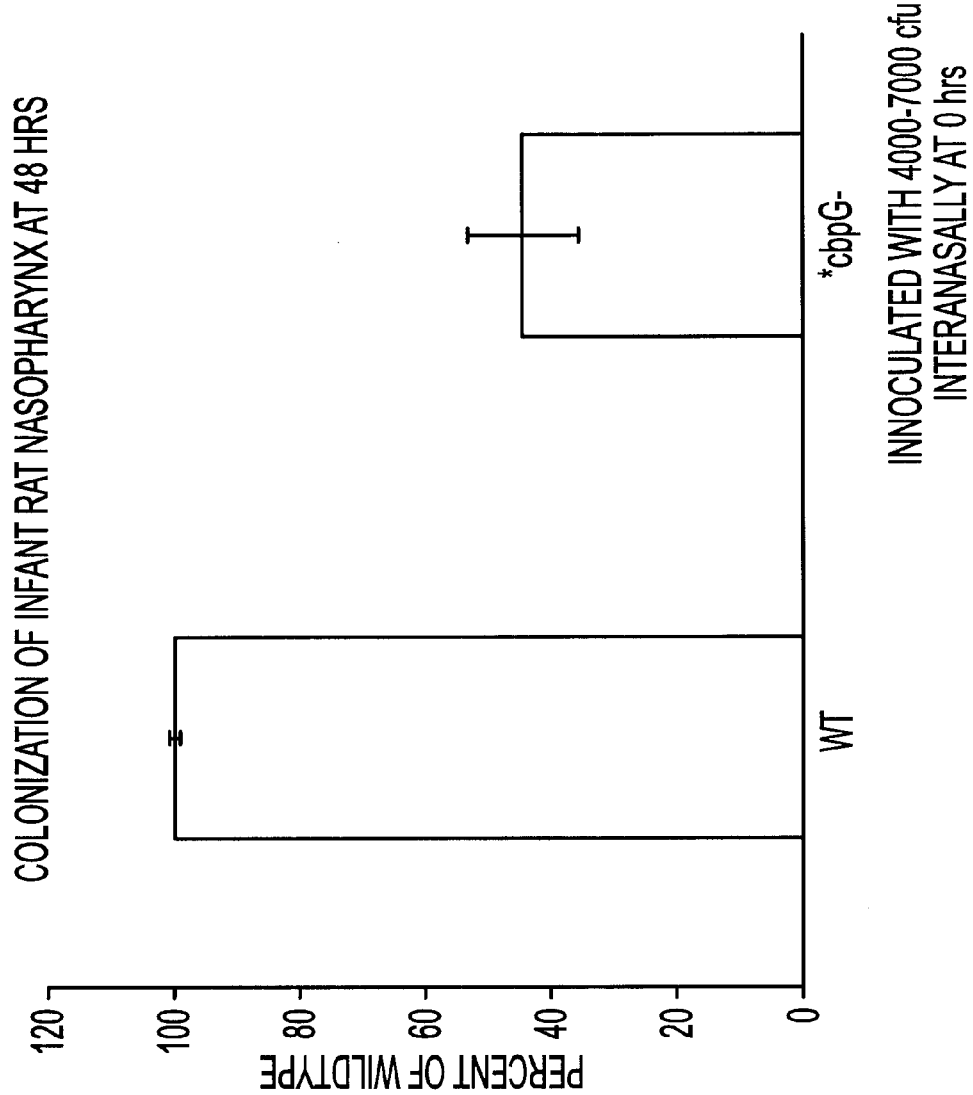
FIG. 5 depicts the effect of the cbpG knockout, generated by insertion duplication mutagenesis, on colonization of infant rat nasopharynx at 48 hours by the method of Weiser, et al (Weiser J N et al (1994) 62(6):2582–2589). WT depicts the colonization of wild type Type 4. Each bar presents the mean of four experiments on 10 rat pups per group.

The effect of the CbpG knockout mutant on colonization of infant rat nasopharynx at 48 hrs is presented graphically in FIG. 5.

TABLE 1

Effect of CbpG deletion on intranasal virulence

| | | wild type (cfu/lavage ± SD) | | | CbpG knockout (cfu/lavage ± SD) | |
|---|---|---|---|---|---|---|
| Exp | n | 48 hr | 96 hr | n | 48 hr | 96 hr |
| 1 | 8 | 529 (±180) | 402 (±159) | 8 | 188 (±118) 0.0007 (35%) | 174 (±86) 0.004* (43%)** |
| 2 | 10 | 306 (±199) | 386 (±308) | 8 | 89 (±55) 0.006 (29%) | 233 (±116) 0.003 (60%) |
| 3 | 12 | 460 (±55) | 332 (±94) | 9 | 117 (±54) (25%) | 163 (±75) 0.003 (49%) |
| 4 | 10 | 244 (±85) | nd | 8 | 23 (±17) 0.00001 (9%) | nd |

*= P value
**= % of wild type
nd = not done

We have tested the ability of this mutant to adhere to human Detroit cells, and to carbohydrates in vitro. The in vitro adhesion experiments were done as previously described (Cundell D. R. et al (1995) *Infect Immun* 63(3):757–761) and the data shown in Table 2 indicate that there is a 40% reduction in adhesion to Detroit human nasopharyngeal cell line by the CbpG-deficient mutant and a 80–90% reduction in adhesion to both lacto-N-neotrose (LNnT) and sialylactose in vitro. These data along with the in vivo colonization data suggest that CbpG plays a role in adherence to cells of he nasopharynx and that the binding may occur through sugars on the eukaryotic cells.

TABLE 2

Adherence of CbpG Mutant to Various Substrates

| Exp # | Substrate | OD | TyR | CbpG// TyR | % of Control |
|---|---|---|---|---|---|
| 1 | 6' Sialyl Lactose-HSA (6'SL) | 0.4 | 251 (46.5) | 41 (14.1) | 16 |
| | α, Acid Glycoprotein-HSA (α, AGP) | 0.4 | 311 (48.5) | 38 (8.4) | 12 |

TABLE 2-continued

Adherence of CbpG Mutant to Various Substrates

| Exp # | Substrate | OD | TyR | CbpG// TyR | % of Control |
|---|---|---|---|---|---|
| 2 | α, AGP | 0.7 | 88 (8.0) | 15 (15.1) | 17 |
|   | 6' SL | 0.7 | 254 (52.3) | 38 (13.5) | 15 |
| 3 | 3' Sialyl Lactose-HSA (3'SL) | 0.7 | 201 (67.0) | 90 (41.1) | 45 |
|   | Lacto N-neotetraose-HSA (LNnT) | 0.7 | 222 (82.6) | 39 (23.5) | 18 |
| 4 | 3' SL | 0.4 | 155 (18.5) | 25 (17.4) | 16 |
|   | LNnT | 0.4 | 190 (92.1) | 27 (11.0) | 14 |
| 5 | 3' SL | 0.7 | 614 (277.8) | 67 (35.3) | 11 |
|   | LNnT | 0.7 | 139 (12.3) | 71 (10.0) | 51 |
| 6 | LNnT | 0..5 | 1107 (344.2) | 166 (24.5) | 15 |
|   | 3' SL | 0.5 | 1057 (216.2) | 114 (37.6) | 11 |
| 7 | LNnT | 0.4 | 52 (17.5) | 13 (4.6) | 25 |
| 8 | Detroit cells | 0.5 | 248 (38) | 219 (98) | 88 |
| 9 | Detroit cells | 0.5 | 437 (117.5) | 177 (34.6) | 41 |
| 10 | Detroit cells | 0.5 | 202 (24.5) | 56 (13) | 27 |

Figure 6:
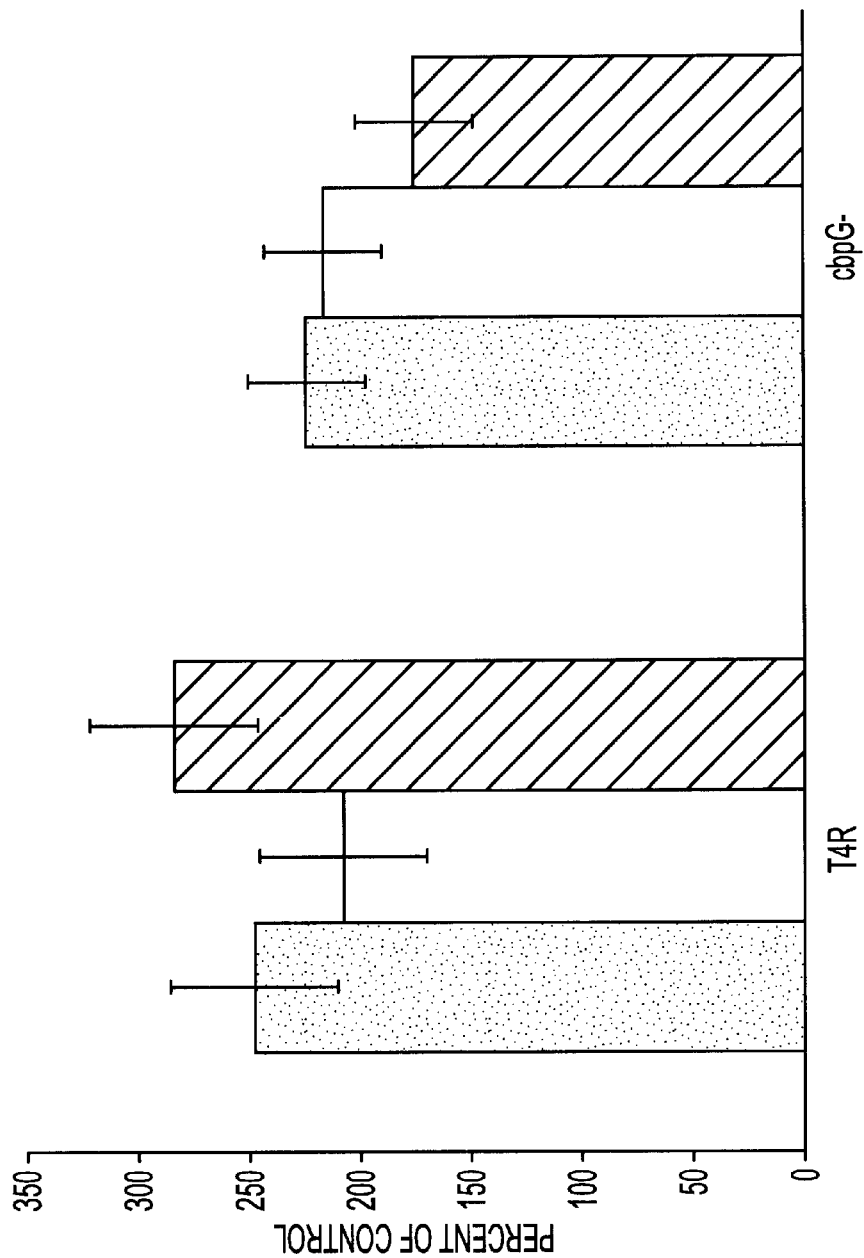
FIG. 6 is a graph of the CbpG knockout in a Type4R (T4R) genetic background (T4R is mutant Type4 pneumococcal strain which is unencapsulated) on the adhesion characteristics of Type 4R mutants on Detroit Nasopharyngeal Human Cell Line. T4R and the CbpG knockout are indicated (T4R and then cbpG−). Each bar represents an individual experiment shown as the mean of four wells.

Substrate Key
TyR → Parent *S. pneumoniae* strain Type 4 Rough
3' Sialyl Lactose-HSA → 3' SL
6' Sialyl Lactose-HSA → 6' SL
Lacto N-neotetraose-HSA → LNnT
Detroit 562 Nasopharyngeal Cell Line → Detroit The effect of the cbpG mutant on the adhesion characteristics of Type 4R mutants on Detroit Nasopharyngeal Human Cells is graphically presented in FIG. 6.

To rule out an activity of CbpG similar to the choline binding protein LytA, the response of the CbpG-deficient mutant (cbpG) to penicillin was determined. There were no differences between the CbpG-deficient mutant and it's isogenic parental strain Type 4 in autolysin dependent lysis in response to the detergent DOC or penicillin or in efficiency of genetic transformation.

Cloning and Purification of CBPG

The coding sequence of cbpG was amplified using primers to sequences immediately downstream of the AUG start codon, CbpGpura (5' CGC GGA TCC GCG TAT ACA GAT AAG AAA CAA G) (SEQ ID NO:7) and sequences overlapping the TAA termination codon, CbpGpurb (5'TCC CCC GGG GAA CAT TAA ATC CAC TCA (SEQ ID NO:8)). These primers amplify out the entire CbpG coding sequence with the exception of the start codon and introduce a BamHi site at the N-terminus of the gene and a SmaI site at the C-terminus of the gene. The PCR product was then digested with BamHI and SmaI and cloned into a pQE30 His-tag expression vector from Qiagen and transformed into *E.coli* strain M15. This results in an in frame fusion of the N-terminus of the CbpG gene with the 6XHis tag of the plasmid. The protein is then purified using a Nickel column following the Qiagen protocol.

100 ml of culture of *E.coli* containing the CbpG expressing plasmid was grown to $OD_{620}$ of 0.7–0.9 and induced with 1.5 mM IPTG. The bacterial pellet was lysed overnight in 20 ml of lysis buffer (6M GuHCl, 0.1M $NaH_2PO4$, 0.01M Tris-Cl, pH8). Sample was centrifuged at 10.000 g for 20 minutes at 4 degrees and the supernatant was collected and filtered through a 0.45 micron filter. 1.5 ml of the NINTA resin was added per 10 ml of sample and mixed gently at room temperature for 1 hr. The mixture was transferred to a small column and washed with 25–30 ml of washing buffer (8M Urea, 0.1M $NaH_2PO_4$, 0.01M Tris-Cl, 20 mM imidazole, pH8). Column was eluted with four 500 µl fractions of elution buffer (8M Urea, 0.1M $NaH_2PO_4$, 0.01M Tris-Cl, 200 nN imidazole pH8).

This procedure resulted in relatively pure protein with minor contaminating bands. This preparation was further separated on a 10% acrylamide gel and a band migrating at 20 kDa, slightly larger than the predicted 17 kDa, was excised and utilized for antibody production in rabbits (Covance Inc). Polyclonal antibodies against the protein recognize the recombinant protein (FIG. 4). These antibodies do not react well with the native CbpG protein in a choline binding protein preparation derived from Type 4. The recombinant protein and the native 17 kD protein from pneumococcus eluted with 10% choline do not react with the antibody described by Rosenow et al. (Rosenow, C. et al. (1997) *Mol Microbiol* 25:819–829).

Construction of CbpG N-terminal Truncate

The N-terminus of CbpG was amplified from T4 chromosomal DNA by PCR using oligos B939f2 (5'-CGCGGATCCTATACAGATAAGAAACAAGTTTTAAGT) (SEQ ID NO:13) and B939r2 (5'-CGCGGTACCATGTTGTCTATAATGGTACCAACTACC) SEQ ID NO:14). The amplified fragment consisted of CbpG amino acids 1–90, deleting the C-terminal choline binding domain, and thus generating an N-terminal CbpG truncate. The amino acid sequence (SEQ ID NO:11) and nucleic acid sequence (SEQ ID NO:12) of the N-terminal truncate of CbpG (amino acids 1–90) is depicted in FIG. 8. The oligos used introduced a BamHI site to the N-terminus of the gene and a KpnI site to the C-terminus. The PCR product was then digested with Bam HI and KpnI. The digested fragment was ligated into a Qiagen pQE-30 6-His tag expression vector and transformed into competent M15 *E. Coli* cells. Clones were screened by restriciton enzyme digestion with BamHI and KpnI. The clones positive for the CbpG truncted insert were sequenced to confirm an in-frame fusion between the His-tag and CbpG truncate coding region.

A 50 ml culture of pQE939nt was grown in 1×LB/Amp/Kan to an $OD_{600}$ of 0.7. The culture was induced with 1.5 mM IPTG and grown for an additional 2 hours. The induced cells were harvested by centrifugation and lysed under native and denatured conditions in order to determine protein expression and solubility. A 15% Tris-HCl gel showed that the 13.2 kDa protein was soluble (FIG. 9a). The protein was purified under denatured conditions with 8M Urea using the His tag over a nickel column. The resulting purified CbpG truncate protein was run on a 15% Tris-HCl gel FIG. 9b, the bands excised, and utilized for antibody production in rabbits (Covance Inc.).

Antibodies Raised Against CbpG are Protective

The polyclonal antibody raised against CbpG (described above) was used in experiments to test its ability to protect against challenge by *S. pneumoniae* in in vivo models of bacterial nose colonization and sepsis as described below in Materials and Methods. The anti-CbpG antibody did not provide protection in a nose colonization test. In the sepsis model, in one experiment, at 24 hours, 6 of 9 animals injected with anti-CbpG antibody were dead versus 8 of 9 animals injected with pre-immune serum. In a second experiment, at 24 hours, 7 of 12 animals injected with anti-CbpG antibody were dead versus 9 of 12 animals injected with pre-immune serum. As noted above, the polyclonal antibodies against CbpG recognize the recombinant protein but do not react well with the native CbpG protein.

FIG. 7 presents a tabulation of the overall results of the experiments characterizing CbpG.

Materials and Methods

The following details the material and methods used in the above described experimental examples:

Strains of *pneumococci* and growth conditions

*S. pneumoniae* type 4 is a clinical isolate obtained from MedImmune Inc. *S. pneumoniae* strain R6x (Tiraby et al (1973) *Proc Natl Acad Sci USA* 70:3541–3545) was obtained from the Rockefeller University collection. *S. pneumoniae* type 4R is an unencapsulated mutant of Type 4 which was constructed by insertion duplication mutagenesis of capsule genes of Type4. *S. pneumoniae* was plated on tryptic soy agar (TSA, Difco, Detroit, Mich., USA) supplemented with sheep blood 3% (v/v). For growth in liquid culture, the bacteria were grown without aeration at 37° C. in 5% $CO_2$ in a semi-synthetic casein hydrolysate medium supplemented with yeast extract (C+Y medium, (Lacks, S and Hotchkiss, R. D. (1960) *Biochem Biophys* Acta 39:508–517). For the selection and maintenance of pneumococci containing chromosomally integrated plasmids, bacteria were grown in the presence of 1 $\mu$g/ml erythromycin (Sigma, St. Louis, Mo., USA).

Recombinant DNA Methods

DNA ligations, restriction endonuclease digestion and gel electrophoresis were performed according to standard protocols (Sambrook, J., Fritsh, E. F. and Maniatis, T. eds. (1989) *Molecular Cloning: A Laboratory Manual* (Second Edition) Cold Spring Harbor Laboratory Press, Cold Spring Harbor, N.Y.). DNA purification and plasmid preparations were performed with kits from Qiagen and Wizard according to the manufacturer's instructions. Plasmids were introduced into *E. coli* strains by chemical transformation. Transformation in *S. pneumoniae* was performed according to standard protocols (Pearce et al (1993) *Mol Microbiol* 9:1037–1050).

Bacterial adhesion assay. The Detroit human nasopharyngeal cell line (American Type Culture Collection) was cultured in ATCC Vitacell Minimal Essential Eagle medium (ATCC Cat#30-2003) supplemented with Earles balanced salt solution, nonessential amino acids, 1 mM sodium pyruvate, 2 mM L-glutamine and 1500 mg sodium bicarbonate. Cells were grown to confluence in Corning 100 mm tissue culture dishes. At confluence, the cells were prepared for subculture with trypsin-0.05 % EDTA (Sigma), washed and resuspended in 5 mls of the above media +10% FBS (Sigma). 10 ul of the resuspended cells were added to Terasaki wells (Robbins Scientific, Sunnyvale, Calif.) and allowed to grow until a confluent monolayer formed. Prior to the adherence assay, culture fluid was removed by washing the monolayers twice with tissue culture medium.

Bacteria at an $OD_{620}$ of 0.4 or 0.6 were washed in 1 ml carbonate buffer (0.05 M sodium carbonate, 0.1 M sodium chloride), resuspended in the same buffer and labeled with FITC (Sigma; 1 mg $ml^{-1}$) for 20 min in the dark at room temperature (LO). After 3 washes with carbonate buffer, the bacteria were resuspended in medium M199 without antibiotics and $5 \times 10^7$ pneumococci were incubated per well for 30 min at 37° C. in the presence of 5% $CO_2$. After the removal of unbound bacteria by washing the monolayers five times with M199, the cells and bacteria were fixed in 2.5% glutaraldehyde for 3 min and washed five times with PBS. Adherent pneumococci were counted visually with an inverted microscope (Diaphot-TDM; Nikon Inc., Melville, N.Y.) equipped for epifluorescence with an IF DM-510 filter and expressed as the number of attached bacteria per 100 lung cells. Values for 6–9 wells were averaged and each experiment was performed 3–6 times.

To test the ability of the mixture of CBPs to affect adherence to eucaryotic cells, the assay is modified such that monolayers are plated in 96 well dishes (Falcon) coated with 0.2% gelatin and at confluence are incubated with a range of concentrations of the mixture of CBPs (1 $\mu$g to 1 mg $ml^{-1}$) for 15 min. After washing, the CBP-treated monolayers are challenged with $5 \times 10^6$ pneumococci for 30 min, washed and adherence is quantitated as fluorescence intensity measured in a Cytofluor II (Perseptive) with excitation at 485 nm and emission at 530 nm.

Adherence to glycoconjugates was assessed by coating Terasaki plates overnight with 100 uM of 6' sialyllactose-HSA, lacto-N-neotetraose-HSA, N-acetylglucosamine-$\beta$1, 4-glucose-HSA or N-acetylglucosamine-$\beta$1,3-glucose-HSA (Neose Inc., Horsham, Pa.). Wells were washed and $1 \times 10^7$ FITC labelled pneumococci were added for 30 min at 37° C. Unbound cells were washed away three times with PBS and adherence was quantitated visually as described above. Each glycoconjugate was tested in 18 wells during three experiments.

Passive protection against systemic challenge. Outbred CF1 mice were housed under specific pathogen free conditions in accordance with institutional and NIH guidelines. Encapsulated pneumococci were grown for 5 hours in C+Y medium and diluted in PBS. Antibody (pre-immune serum for control or postimmune, 0.5 ml diluted 1:10 in PBS) is incubated with the inoculum for 30 min at 37° C. and then the entire mixture is injected. Two groups often mice received an inoculum of $3 \times 10^7$ cfu of Type 4 by injection into the peritoneal cavity. The number of animals alive or dead is scored over 4 days.

Nasopharyngeal challenge. Nasopharyngeal colonization of 1 to 5-day old Sprague-Dawley rats by pneumococci was carried out as described previously using Type4 (Weiser J N et al (1994) 62(6):2582–2589). For each experiment, litters were andomized and sorted into groups of eight to ten pups. Each pup received equal intranasal inocula of $2.5-8 \times 10^3$ cfu in 10 ul of PBS of either the parent strain (Type 4) or the isogenic mutant containing a defined mutation in cbpG. Colonization was assessed at 48 and 96 hours post-inoculation. To insure accurate evaluation of recovered bacteria, the fluid from the nasal washes were diluted in series, plated and colony counts determined. Results are expressed as the geometric mean of each group ±the standard divination (n=20). To determine protective activity of anti-CbpG antisera, the protocol was modified such that the parent strain inoculum was treated with antiserum (pre-immune serum for control or postimmune, 0.5 ml diluted 1:10 in PBS) for 30 min at 37° C. and the mixture inoculated intranasally.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein. Various references are cited throughout this Specification, each of which is incorporated herein by reference in its entirety.

What is claimed is:

1. An isolated streptococcal CbpG choline binding polypeptide comprising the amino acid sequence set out as SEQ ID NO: 2.

2. An N-terminal truncate polypeptide of a choline binding protein (SEQ ID NO:2), wherein the truncated polypeptide comprises the amino acid sequence set out as SEQ ID NO:11.

3. An N-terminal truncate polypeptide of a choline binding protein CbpG, wherein the truncated polypeptide consists of amino acids 1 through 90 of SEQ ID NO:2.

4. The streptococcal choline binding polypeptide of claim 1 or claim 2 labeled with a detectable label.

5. An immunogenic composition comprising a choline binding polypeptide of claim 1 or claim 3 and a pharmaceutically acceptable carrier.

6. The immunogenic composition of claim 5, further comprising at least one active ingredient selected from the group consisting of:
   a. a streptococcal choline binding protein selected from the group of CbpD, CbpE and CbpF;
   b. PspA;
   c. CbpA; and
   d. autolysin (LytA).

* * * * *

UNITED STATES PATENT AND TRADEMARK OFFICE
CERTIFICATE OF CORRECTION

PATENT NO.   : 6,495,139 B2  Page 1 of 1
DATED        : December 17, 2002
INVENTOR(S)  : Tuomanen et al.

It is certified that error appears in the above-identified patent and that said Letters Patent is hereby corrected as shown below:

Column 51,
Line 36, "claim 2" should read -- claim 3 --.

Signed and Sealed this

Tenth Day of June, 2003

JAMES E. ROGAN
*Director of the United States Patent and Trademark Office*

SEQUENCE LISTING

<160> NUMBER OF SEQ ID NOS: 14

<210> SEQ ID NO 1
<211> LENGTH: 179
<212> TYPE: PRT
<213> ORGANISM: Pneumococcus

<400> SEQUENCE: 1

Thr Gly Trp Lys Gln Glu Asn Gly Met Trp Tyr Phe Tyr Asn Thr Asp
 1               5                  10                  15

Gly Ser Met Ala Thr Gly Trp Leu Gln Asn Asn Gly Ser Trp Tyr Tyr
                20                  25                  30

Leu Asn Ser Asn Gly Ala Met Ala Thr Gly Trp Leu Gln Asn Asn Gly
            35                  40                  45

Ser Trp Tyr Tyr Leu Asn Ala Asn Gly Ser Met Ala Thr Gly Trp Leu
    50                  55                  60

Gln Asn Asn Gly Ser Trp Tyr Tyr Leu Asn Ala Asn Gly Ser Met Ala
65                  70                  75                  80

Thr Gly Trp Leu Gln Tyr Asn Gly Ser Trp Tyr Tyr Leu Asn Ala Asn
                85                  90                  95

Gly Ser Met Ala Thr Gly Trp Leu Gln Tyr Asn Gly Ser Trp Tyr Tyr
            100                 105                 110

Leu Asn Ala Asn Gly Asp Met Ala Thr Gly Trp Val Lys Asp Gly Asp
        115                 120                 125

Thr Trp Tyr Tyr Leu Glu Ala Ser Gly Ala Met Lys Ala Ser Gln Trp
    130                 135                 140

Phe Lys Val Ser Asp Lys Trp Tyr Tyr Val Asn Gly Ser Gly Ala Leu
145                 150                 155                 160

Ala Val Asn Thr Thr Val Asp Gly Tyr Gly Val Asn Ala Asn Gly Glu
                165                 170                 175

Trp Val Asn

<210> SEQ ID NO 2
<211> LENGTH: 153
<212> TYPE: PRT
<213> ORGANISM: Pneumococcus
<220> FEATURE:
<221> NAME/KEY: UNSURE
<222> LOCATION: (35)
<223> OTHER INFORMATION: The amino acid can be any of Ile, Thr, Asn, or
      Ser. The DNA coding is AST for this amino acid

<400> SEQUENCE: 2

Met Tyr Thr Asp Lys Lys Gln Val Leu Ser Asp Gly Met Phe Leu
 1               5                  10                  15

Asp Tyr Gln Val Asp Thr Leu Glu Gly Ser Ser Gly Ser Thr Val Tyr
                20                  25                  30

Asp Ala Xaa His Arg Val Val Gly Val His Thr Leu Gly Asp Gly Ala
            35                  40                  45

Asn Gln Ile Asn Ser Ala Val Lys Leu Asn Glu Arg Asn Leu Pro Phe
    50                  55                  60

Ile Tyr Ser Val Leu Lys Gly Tyr Ser Leu Gly Trp Lys Lys Ile
65                  70                  75                  80

Asn Gly Ser Trp Tyr His Tyr Arg Gln His Asp Lys Gln Thr Gly Trp
                85                  90                  95

Gln Glu Ile Asn Asp Thr Trp Tyr Tyr Leu Asp Ser Ser Gly Lys Met

```
                100             105             110
Leu Thr Asp Trp Gln Lys Val Asn Gly Lys Trp Tyr Tyr Leu Asn Ser
            115                 120                 125
Asn Gly Ala Met Val Thr Gly Ser Gln Thr Ile Asp Gly Lys Val Tyr
    130                 135                 140
Asn Phe Ala Ser Ser Gly Glu Trp Ile
145                 150

<210> SEQ ID NO 3
<211> LENGTH: 462
<212> TYPE: DNA
<213> ORGANISM: Pneumococcus

<400> SEQUENCE: 3
atgtatacag ataagaaaca agttttaagt gatgatggca tgttcttgga ttaccaagtt      60
gatactttag agggtctag tggatctaca gtttatgatg ctastcaccg tgtagtagga     120
gtgcatactt taggagatgg agctaatcaa attaacagtg cagttaaatt aaatgaacga     180
aatttgccat ttatttattc ggttcttaaa ggttactctc ttgaaggatg aagaaaata     240
aatggtagtt ggtaccatta tagacaacat gataaacaaa cgggttggca ggagataaat     300
gatacttggt attatttaga cagttccggt aagatgctta cagattggca aaagtaaat     360
ggaaaatggt attatctcaa ttcaaatgga gcaatggtta caggtagcca aactatcgat     420
ggtaaagttt ataacttcgc ttcatctggt gagtggattt aa                       462

<210> SEQ ID NO 4
<211> LENGTH: 1889
<212> TYPE: DNA
<213> ORGANISM: Pneumococcus

<400> SEQUENCE: 4
ctgcgaattt tattaaagat aatgtgttaa ttacagcggc tcacaactac tacagacatg       60
actatgggaa agaagcggat gatatttatg ttcttccggc tgttagtcca agtcaagaac     120
catttggaaa gatcaaagta aggaagttc gttatttgaa ggaatttaga aatttaaatt     180
ctaaggatgc aagggaatat gacttggctt tattaattct agaagagccc attggtgcaa     240
aattagggac tttgggtctt cctactagtc aaaaaaattt gacaggaata actgtgacta     300
tcacaggcta tccatcatat aattttaaaa ttcatcaaat gtatacagat aagaaacaag     360
ttttaagtga tgatggcatg ttcttggatt accaagttga ctttagag gggtctagtg     420
gatctacagt ttatgatgct astcaccgtg tagtaggagt gcatacttta ggagatggag     480
ctaatcaaat taacagtgca gttaaattaa atgaacgaaa tttgccattt atttattcgg     540
ttcttaaagg ttactctctt gaaggatgga agaaaataaa tggtagttgg taccattata     600
gacaacatga taaacaaacg gttggcagga gataaatga tacttggtat atttagaca     660
gttccggtaa gatgcttaca gattggcaaa agtaaatgg aaaatggtat tatctcaatt     720
caaatggagc aatggttaca ggtagccaaa ctatcgatgg taaagtttat aacttcgctt     780
catctggtga gtggatttaa tgttggagga tatataaaat gaagcttttg aaaaaaatga     840
tgcaaatcgc actagccaca tttttcttcg gtttgttagc gacaaataca gtatttgcag     900
atgattctga aggatggcag tttgtccaag aaaatggtag aacctactac aaaaaggggg     960
atctaaaaga aacctactgg agagtgatag atgggaagta ctattatttt gatcctttat    1020
ccggagagat ggttgtcggc tggcaatata tacctgctcc acacaagggg gttacgattg    1080
```

-continued

```
gtccttctcc aagaatagag attgctctta gaccagattg gttttatttt ggtcaagatg   1140
gtgtattaca agaatttgtt ggcaagcaag ttttagaagc aaaaactgct acgaatacca   1200
acaaacatca tggggaagaa tatgatagcc aagcagagaa acgagtctat tattttgaag   1260
atcagcgtag ttatcatact ttaaaaactg gttggattta tgaagagggt cattggtatt   1320
atttacagaa ggatggtggc tttgattcgc gcatcaacag attgacggtt ggagagctag   1380
cacgtggttg ggttaaggat taccctctta cgtatgatga agagaagcta aaagcagctc   1440
catggtacta tctaaatcca gcaactggca ttatgcaaac aggttggcaa tatctaggta   1500
atagatggta ctacctccat cgtcaggag ctatggcaac tggctggtat aaggaaggct   1560
caacttggta ctatctagat gctgaaaatg gtgatatgag aactggctgg caaaaccttg   1620
ggaacaaatg gtactatctc cgttcatcag gagctatggc aactggttgg tatcaggaaa   1680
gttcgacttg gtactatcta aatgcaagta atggagatat gaaaacaggc tggttccaag   1740
tcaatggtaa ctggtactat gcctatgatt caggtgcttt agctgttaat accacagtag   1800
gtggttacta cttaaactat aatggtgaat gggttaagta atgaaggcta attgtaaact   1860
gtgatggata cttaactttg tataatagg                                      1889
```

<210> SEQ ID NO 5
<211> LENGTH: 26
<212> TYPE: DNA
<213> ORGANISM: Pneumococcus

<400> SEQUENCE: 5
ttcttgaatt cccaagttga tacttt                                          26

<210> SEQ ID NO 6
<211> LENGTH: 28
<212> TYPE: DNA
<213> ORGANISM: Pneumococcus

<400> SEQUENCE: 6
ataatggatc caactaccat ttattttc                                        28

<210> SEQ ID NO 7
<211> LENGTH: 31
<212> TYPE: DNA
<213> ORGANISM: Pneumococcus

<400> SEQUENCE: 7
cgcggatccg cgtatacaga taagaaacaa g                                    31

<210> SEQ ID NO 8
<211> LENGTH: 27
<212> TYPE: DNA
<213> ORGANISM: Pneumococcus

<400> SEQUENCE: 8
tcccccgggg aacattaaat ccactca                                         27

<210> SEQ ID NO 9
<211> LENGTH: 20
<212> TYPE: PRT
<213> ORGANISM: Pneumococcus

<400> SEQUENCE: 9

Gly Trp Leu Lys Asp Asn Gly Ser Trp Tyr Tyr Leu Asn Ala Asn Gly
 1               5                   10                  15

```
Ala Met Ala Thr
            20

<210> SEQ ID NO 10
<211> LENGTH: 508
<212> TYPE: DNA
<213> ORGANISM: Pneumococcus

<400> SEQUENCE: 10
tgtgactatc acaggctatc catcatataa ttttaaaatt catcaaatgt atacagataa      60
gaaacaagtt ttaagtgatg atggcatgtt cttggattac caagttgata ctttagaggg     120
gtctagtgga tctacagttt atgatgctas tcaccgtgta gtaggagtgc atactttagg     180
agatggagct aatcaaatta acagtgcagt taaattaaat gaacgaaatt tgccatttat     240
ttattcggtt cttaaaggtt actctcttga aggatggaag aaaataaatg gtagttggta     300
ccattataga caacatgata acaaacggg ttggcaggag ataaatgata cttggtatta     360
tttagacagt tccggtaaga tgcttacaga ttggcaaaaa gtaaatggaa atggtatta     420 tctcaattca aatggagcaa tggttacagg tagccaaact atcgatggta agtttataa     480 cttcgcttca tctggtgagt ggatttaa                                       508

<210> SEQ ID NO 11
<211> LENGTH: 90
<212> TYPE: PRT
<213> ORGANISM: Pneumococcus
<220> FEATURE:
<221> NAME/KEY: UNSURE
<222> LOCATION: (35)
<223> OTHER INFORMATION: The DNA code for this amino acid is AST, and
      the amino acid can be any of Ile, Thr, Asn, or Ser.

<400> SEQUENCE: 11

Met Tyr Thr Asp Lys Lys Gln Val Leu Ser Asp Asp Gly Met Phe Leu
 1               5                  10                  15

Asp Tyr Gln Val Asp Thr Leu Glu Gly Ser Ser Gly Ser Thr Val Tyr
                20                  25                  30

Asp Ala Xaa His Arg Val Val Gly Val His Thr Leu Gly Asp Gly Ala
            35                  40                  45

Asn Gln Ile Asn Ser Ala Val Lys Leu Asn Glu Arg Asn Leu Pro Phe
        50                  55                  60

Ile Tyr Ser Val Leu Lys Gly Tyr Ser Leu Glu Gly Trp Lys Lys Ile
 65                 70                  75                  80

Asn Gly Ser Trp Tyr His Tyr Arg Gln His
                85                  90

<210> SEQ ID NO 12
<211> LENGTH: 270
<212> TYPE: DNA
<213> ORGANISM: Pneumococcus

<400> SEQUENCE: 12
atgtatacag ataagaaaca agttttaagt gatgatggca tgttcttgga ttaccaagtt      60
gatactttag agggtctag tggatctaca gtttatgatg ctastcaccg tgtagtagga     120
gtgcatactt taggagatgg agctaatcaa attaacagtg cagttaaatt aaatgaacga     180
aatttgccat ttatttattc ggttcttaaa ggttactctc ttgaaggatg gaagaaaata     240
aatggtagtt ggtaccatta tagacaacat                                     270
```

```
<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 13
cgcggatcct atacagataa gaaacaagtt ttaagt                               36

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 14
cgcggtacca tgttgtctat aatggtacca actacc                               36
```